United States Patent
Burnett, Jr. et al.

(10) Patent No.: US 9,115,209 B2
(45) Date of Patent: Aug. 25, 2015

(54) METHOD OF TREATMENT OF CARDIOVASCULAR OR RENAL CONDITIONS WITH NATRIURETIC POLYPEPTIDES WITH UNIQUE PHARMACOLOGIC PROFILES

(71) Applicant: Mayo Foundation for Medical Education and Research, Rochester, MN (US)

(72) Inventors: John C. Burnett, Jr., Rochester, MN (US); Candace Y. W. Lee, Saint-Leonard (CA)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/257,552

(22) Filed: Apr. 21, 2014

(65) Prior Publication Data
US 2014/0228294 A1 Aug. 14, 2014

Related U.S. Application Data

(62) Division of application No. 13/002,178, filed as application No. PCT/US2009/047534 on Jun. 16, 2009, now Pat. No. 8,741,842.

(60) Provisional application No. 61/077,824, filed on Jul. 2, 2008.

(51) Int. Cl.
| A61K 38/22 | (2006.01) |
| A61K 38/16 | (2006.01) |
| A61K 38/12 | (2006.01) |
| C07K 14/58 | (2006.01) |
| A61K 38/00 | (2006.01) |

(52) U.S. Cl.
CPC C07K 14/58 (2013.01); *A61K 38/00* (2013.01)

(58) Field of Classification Search
None
See application file for complete search history.

(56) References Cited

U.S. PATENT DOCUMENTS

| 4,034,074 | A | 7/1977 | Miles |
| 4,098,876 | A | 7/1978 | Piasio et al. |
| 4,233,402 | A | 11/1980 | Maggio et al. |
| 5,296,347 | A | 3/1994 | LaMotte, III |
| 5,580,859 | A | 12/1996 | Feigner et al. |
| 5,589,466 | A | 12/1996 | Feigner et al. |
| 7,754,852 | B2 | 7/2010 | Burnett, Jr. et al. |
| 2011/0152191 | A1 | 6/2011 | Burnett |

OTHER PUBLICATIONS

Ausubel et al., Ed., "Immunology," *Short Protocols in Molecular Biology*, Unit 11, Green Publishing Associates and John Wiley & Sons, 56 pages, 1992.

Ausubel et al., Ed., "Mutagenesis of Cloned DNA," *Short Protocols in Molecular Biology*, Unit 8, Green Publishing Associates and John Wiley & Sons, 26 pages, 1992.

Boerrigter et al., "Abstract 3478: Evidence for Differential Modulation of the Cardiorenal Actions of B-Type Natriuretic Peptide by the Peptidases Dipeptidyl Peptidase IV and Meprin A," *Circulation*, 118:S_432, 2008.

Burnett et al., "Atrial natriuretic peptide elevation in congestive heart failure in the human," *Science*, 231(4742):1145-1147, Mar. 1986.

Burnett et al., "Effects of synthetic atrial natriuretic factor on renal function and renin release," *Am. J. Physiol.*, 247(5 Pt 2):F863-866, Nov. 1984.

Cataliotti et al., "Abstract 6278: Burden of Chronic Renal Insufficiency in the General Population and Added Predictive Power of GFR to BNP and NT-proBNP in Detection of Altered Ventricular Structure and Function," *Circulation*, 118:S_1173, 2008.

Cataliotti et al., "CNP production in the kidney and effects of protein intake restriction in nephrotic syndrome," *Am. J. Physiol.*, 283(3):F464-472, Sep. 2002.

Cataliotti, "Chronic Actions of a Novel Oral B-Type Natriuretic Peptide Conjugate in Normal Dogs and Acute Actions in Angiotensin II—Mediated Hypertension," *Circulation*, 118:1729-1736 Epub Oct. 6, 2008.

Chaurand et al., "Peptide and protein identification by matrix-assisted laser desorption ionization (MALDI) and MALDI-post-source decay time-of-flight mass spectrometry," *J. Am. Soc. Mass Spectrom.*, 10(2):91-103, Feb. 1999.

Chen et al., "Abstract 1481: Renal Targeted Protein Therapeutics in Experimental Overt Heart Failure With Renal Dysfunction," *Circulation*, 118:S_334, 2008.

Chen et al., "Equimolar doses of atrial and brain natriuretic peptides and urodilatin have differential renal actions in overt experimental heart failure," *Am. J. Physiol. Regul. Integr. Comp. Physiol.*, 288(5):R1093-1097, print May 2005, epub Dec. 2004.

Cole et al., "Monoclonal Antibodies and Cancer Therapy," Alan R. Liss, Inc., pp. 77-96 (1983).

Cote et al., "Generation of human monoclonal antibodies reactive with cellular antigens," *Proc. Natl. Acad. Sci. USA*, 80(7):2026, Apr. 1983.

Cowie and Mendez, "BNP and congestive heart failure," *Prog Cardiovasc Dis.*, 44(4):293-321, Jan.-Feb. 2002.

Gevaert et al., "Protein identification based on matrix assisted laser desorption/ionization-post source decay-mass spectrometry," *Electrophoresis*, 22(9):1645-1651, May 2001.

Guatelli et al., "Isothermal, in vitro amplification of nucleic acids by a multienzyme reaction modeled after retroviral replication," *Proc. Natl. Acad. Sci. USA*, 87(5):1874-1878, Mar. 1990.

(Continued)

*Primary Examiner* — Elly-Gerald Stoica
(74) *Attorney, Agent, or Firm* — Fish & Richardson P.C.

(57) ABSTRACT

This document provides natriuretic polypeptides. For example, this document provides polypeptides having a natriuretic activity. In some cases, a polypeptide provided herein can have natriuretic activities without inducing excessive hypotension. This document also provides methods and materials for inducing natriuretic activities within a mammal.

14 Claims, 37 Drawing Sheets

(56) References Cited

OTHER PUBLICATIONS

Haber et al., "Application of a radioimmunoassay for angiotensin I to the physiologic measurements of plasma renin activity in normal human subjects," J. Clin. Endocrinol. Metab., 29(10):1349-1355, Oct. 1969.
Huse et al., "Generation of a large combinatorial library of the immunoglobulin repertoire in phage lambda," Science, 246(4935):1275-1281, Dec. 1989.
Hyrup and Nielsen, "Peptide nucleic acids (PNA): synthesis, properties and potential applications," *Bioorgan. Med. Chem.*, 4(1):5-23, Jan. 1996.
Köhler and Milstein, "Continuous cultures of fused cells secreting antibody of predefined specificity," *Nature*, 256(5517):495-497, Aug. 1975.
Kozbor et al., "The production of monoclonal antibodies from human lymphocytes," *Immunology Today*, 4(3):72-79, Mar. 1983.
Lee and Burnett Jr., "Design, synthesis and in vivo actions of a novel designer natriuretic peptide, BUA-NP," *J Clin Pharmacol.*, 48(9):1133. [presented as a poster] Thirty-Seventh Annual Meeting of the American College of Clinical Pharmacology in Philadelphia, PA on Sep. 15, 2008.
Lee and Burnett Jr., "Design, synthesis, and cardiorenal actions of a novel peptide, CDD-NP," *J Clin Pharmacol*, 48(9):1132, Abstract 143, Sep. 2008.
Lee and Burnett Jr., "Design, synthesis, and in vivo pharmacologic actions of a novel designer natriuretic peptide fusing human atrial natriuretic peptide and human B-type natriuretic peptide," *Can J Cardiol.*, vol. 24 Suppl E, p. 85E, [presented as a poster] presented at The Canadian Cardiovascular Congress in Toronto, Canada on Oct. 26, 2008.
Lee and Burnett Jr., "Pharmacodynamics of a novel designer natriuretic peptide, BUA-NP, in normal anesthetized dogs," Pulsus [online] 2009 [retrieved on Dec. 11, 2013]. Retrieved from the Internet: < URL: http://www.pulsus.com/ccc2009/abs/701.htm>, 1 page, Canadian Cardiovascular Congress, 62nd Annual Meeting of the Canadian Cardiovascular Society, 2009.
Lee and Burnett, "Engineered mutation of human B-type natriuretic peptide to preserve renal perfusion pressure," *J Card Fail.*, 14(6) Suppl: S3-S4, Aug. 2008. Presented as an oral presentation at The 12$^{th}$ Annual Scientific Meeting of the Heart Failure Society of America in Toronto, Canada on Sep. 22, 2008.
Lee and Burnett, Jr., "Design, synthesis and in vivo actions of a novel designer natriuretic peptide, BUA-NP," *J Clin Pharmacol*, 48(9):1132, Abstract 147, Sep. 2008.
Lee et al., "A first-in-human clinical trial of a novel chimeric natriuretic peptide, CD-NP, in healthy subjects," *Eur Heart J*, 29(Abstract Supplement):299, Abstract 1949, 2008.
Lee et al., "Abstract 1485: Tissue Specific Activation of cGMP by an Alternatively Spliced Form of BNP," *Circulation*, 118:S_335, 2008.
Lee et al., "Abstract 1497: A Novel Designer Natriuretic Peptide, CAA-NP, As Assessed in Human Aortic Endothelial Cells: Evidence for Involvement of Natriuretic Peptide Receptor-A (NPR-A) and NPR-B in Cyclic GMP Response," *Circulation*, 118:S_337-S_338, 2008.
Lee et al., "Abstract 371: Cardiorenal and Neurohumoral Actions of a Novel Designer Natriuretic Peptide, CU-NP, in Canine Experimental Heart Failure," *Circulation*. 2008;118:S_293, 2008.
Lee et al., "Abstract 5432: Mutation of Three Amino Acids in the Disulfide-Ring of a CNP Based Chimeric Natriuretic Peptide Alters its Vascular Properties," *Circulation*, 118:S_549, 2008.
Lee et al., "Abstract P140: A Novel New Generation Designer Natriuretic Peptide, CBB-NP, Exerts Favorable Cardiorenal and Neurohumoral Actions," *Circulation*, 118:S_1475, 2008.
Lee et al., "Cyclic GMP stimulating actions of two novel peptides, CU-NP and CNP-C, as assessed in isolated canine glomeruli," *J Clin Pharmacol*, 48(9):1133, Abstract 145, Sep. 2008.
Lee et al., "Design, synthesis and cardiorenal actions of two novel peptides derived from human B-type natriuretic peptide" ICRH's Young Investigators Forum, May 21-23, 2009, p. 8, Retrieved from the Internet: <URL: http://www.f2fe.com/yiforum/2009/fwyi09/5a-%20Poster%20Abstracts%20Day%201.pdf>, 1 page.
Lee et al., "Evaluation of a novel designer peptide, CU-NP, in human aortic endothelial cells and in vivo" *J Clin Pharmacol*, 48(9):1132, Abstract 144, Sep. 2008.
Lee et al., "Hemoconcentrating effects of two novel designer natriuretic peptides, CU-NP and CBB-NP," *J Clin Pharmacol*, 48(9):1133, Abstract 146, Sep. 2008.
Lee et al., "Pharmacodynamics of a novel designer natriuretic peptide, CD-NP, in a first-in-human clinical trial in healthy subjects," *J Clin Pharmacol.*, 49(6):668-673, Epub Apr. 2009.
Lee et al., "Renal Cyclic GMP Stimulating Actions of a Novel Chimeric Natriuretic Peptide CD-NP in Isolated Glomeruli: Evidence for NPR-A Activation," Journal of Cardiac Failure, 14(6): S11, Abstract 028, Aug. 2008, 12th Annual Scientific Meeting, Heart Failure Society of America, (HFSA), Sep. 21-24, 2008, Toronto, Ontario, Canada, 1 page.
Lee, "Engineered Mutation of Human B-Type Natriuretic Peptide to Preserve Renal Perfusion Pressure," [oral presentation slides] Jay N. Cohn New Investigator Clinical/Integrative Physiology Award Competition, The Annual Scientific Meeting of the Heart Failure Society of America, Sep. 22, 2008, 24 pages.
Lewis, "PCR's Competitors Are Alive and Well and Moving Rapidly Towards Commercialization," Genetic Engineering News, 12(9):1, 3 pages, Jun. 1992.
Lisy et al., "Design, Synthesis, and Actions of a Novel Chimeric Natriuretic Peptide: CD-NP," *J Am Coll Cardiol.*, 52(1): 60-68, Jul. 2008.
Luchner et al., "Angiotensin II in the evolution of experimental heart failure," *Hypertension*, 28(3):472-477, Sep. 1996.
Margulies et al., "Angiotensin inhibition potentiates the renal responses to neutral endopeptidase inhibition in dogs with congestive heart failure," *J. Clin. Invest.*, 88(5):1636-1642, Nov. 1991.
Martin et al., "Abstract 1484: New Insights into the Kidney-Heart Connection: Mild Renal Insufficiency Induces Cardiac Fibrosis and Diastolic Dysfunction Followed by Late Systolic Impairment," *Circulation*, 118:S_334-S_335, 2008.
Osman et al., "Molecular identification and immunohistochemical localization of atrial natriuretic peptide in the heart of the dromedary camel (*Camelus dromedarius*)." *Comp Biochem Physiol A Mol Integr Physiol.*, 139(4):417-424, Dec. 2004.
Sancho and Haber, "A direct microassay for aldosterone in plasma extracts," *J. Clin. Endocrinol. Metab.*, 47(2):391-396, Aug. 1978.
Steiner et al., "Radioimmunoassay for cyclic nucleotides. I. Preparation of antibodies and iodinated cyclic nucleotides," *J. Biol. Chem.*, 247(4):1106-1113, Feb. 1972.
Summerton and Weller, "Morpholino antisense oligomers: design, preparation, and properties," *Antisense Nucleic Acid Drug Dev.*, 7(3):187-195, Jun. 1997.
Supaporn et al., "Blunted cGMP response to agonists and enhanced glomerular cyclic 3',5'-nucleotide phosphodiesterase activities in experimental congestive heart failure," *Kidney Int.*, 50(5):1718-1725, Nov. 1996.
Weiss, "Hot prospect for new gene amplifier," *Science*, 254(5036):1292-1293, Nov. 1991.
European Search Report for Application No. 09774035.1, mailed Aug. 4, 2011, 4 pages.
International Preliminary Report on Patentability for PCT/US2009/047534, mailed Jan. 13, 2011, 6 pages.
International Search Report and Written Opinion for PCT/US2009/047534, mailed Mar. 3, 2010, 13 pages.

Figure 1

The ring structure of BAA-NP consists of the 17 amino acids and the disulfide bond (-S-S-) of the ring structure of human B-type natriuretic peptide The amino- (NH$_2$-) and carboxyl- (COOH-) termini of BAA-NP consist of the AA sequences from the amino- and the carboxyl-termini of human atrial natriuretic peptide.

Figure 2

The ring structure of BUA-NP consists of the 17 amino acids and the disulfide bond (-S-S-) of the ring structure of human B-type natriuretic peptide The amino- (NH$_2$-) and carboxyl- (COOH-) termini of BUA-NP consist of the AA sequences from the amino-terminus of human urodilatin and the carboxyl-terminus of human atrial natriuretic peptide (the latter is the same as the carboxyl-terminus of human urodilatin).

SEQUENCE LISTING

```
<160> NUMBER OF SEQ ID NOS: 7

<210> SEQ ID NO 1
<211> LENGTH: 6
<212> TYPE: PRT
<213> ORGANISM: Homo sapiens

<400> SEQUENCE: 1

Ser Leu Arg Arg Ser Ser
1               5

<210> SEQ ID NO 2
<211> LENGTH: 17
<212> TYPE: PRT
<213> ORGANISM: Homo sapiens

<400> SEQUENCE: 2

Cys Phe Gly Arg Lys Met Asp Arg Ile Ser Ser Ser Ser Gly Leu Gly
1               5                   10                  15

Cys

<210> SEQ ID NO 3
<211> LENGTH: 5
<212> TYPE: PRT
<213> ORGANISM: Homo sapiens

<400> SEQUENCE: 3

Asn Ser Phe Arg Tyr
1               5

<210> SEQ ID NO 4
<211> LENGTH: 28
```

```
<212> TYPE: PRT
<213> ORGANISM: Artificial Sequence
<220> FEATURE:
<223> OTHER INFORMATION: synthetic peptide

<400> SEQUENCE: 4

Ser Leu Arg Arg Ser Ser Cys Phe Gly Arg Lys Met Asp Arg Ile Ser
 1               5                  10                  15

Ser Ser Ser Gly Leu Gly Cys Asn Ser Phe Arg Tyr
            20                  25

<210> SEQ ID NO 5
<211> LENGTH: 32
<212> TYPE: PRT
<213> ORGANISM: Artificial Sequence
<220> FEATURE:
<223> OTHER INFORMATION: synthetic peptide

<400> SEQUENCE: 5

Thr Ala Pro Arg Ser Leu Arg Arg Ser Ser Cys Phe Gly Arg Lys Met
 1               5                  10                  15

Asp Arg Ile Ser Ser Ser Ser Gly Leu Gly Cys Asn Ser Phe Arg Tyr
            20                  25                  30

<210> SEQ ID NO 6
<211> LENGTH: 10
<212> TYPE: PRT
<213> ORGANISM: Homo sapiens

<400> SEQUENCE: 6

Thr Ala Pro Arg Ser Leu Arg Arg Ser Ser
 1               5                  10

<210> SEQ ID NO 7
<211> LENGTH: 5
<212> TYPE: PRT
<213> ORGANISM: Homo sapiens

<400> SEQUENCE: 7

Asn Ser Phe Arg Tyr
 1               5
```

METHOD OF TREATMENT OF CARDIOVASCULAR OR RENAL CONDITIONS WITH NATRIURETIC POLYPEPTIDES WITH UNIQUE PHARMACOLOGIC PROFILES

STATEMENT AS TO FEDERALLY SPONSORED RESEARCH

This invention was made with government support under grant HL036634 awarded by the National Institutes of Health. The government has certain rights in the invention.

CROSS-REFERENCE TO RELATED APPLICATIONS

This application is a divisional of U.S. application Ser. No. 13/002,178, filed Mar. 2, 2011, which is a National Stage application under 35 U.S.C. 371 of International Application No. PCTUS2009/047534, filed Jun. 16, 2009, which claims benefit of priority from U.S. Provisional Application Ser. No. 61/077,824, filed on Jul. 2, 2008.

BACKGROUND

1. Technical Field

This document relates to natriuretic polypeptides. For example, this document provides methods and materials related to natriuretic polypeptides having an improved pharmacologic profile (e.g., reduced ability to induce severe hypotension) and the use of such natriuretic polypeptides to treat or prevent cardiovascular, renal, or metabolic disease conditions such as ischemia heart disease, heart failure, hypertensive heart disease, and renal dysfunction.

2. Background Information

Natriuretic polypeptides are polypeptides that can cause natriuresis (increased sodium excretion in the urine). Such polypeptides can be produced by brain, heart, kidney, and/or vasculature tissue.

SUMMARY

This document relates to natriuretic polypeptides. For example, this document provides methods and materials related to natriuretic polypeptides having an improved pharmacologic profile (e.g., reduced ability to induce severe hypotension) and the use of natriuretic polypeptides to treat or prevent cardiovascular conditions, renal conditions, metabolic disease conditions, or combinations thereof. In some cases, a polypeptide provided herein can have the ability to increase plasma cGMP levels, the ability to increase urinary cGMP excretion, the ability to increase urine flow, the ability to increase urinary sodium excretion, the ability to increase renal blood flow, the ability to alter renal perfusion pressure, the ability to reduce renal vascular resistance, the ability to reduce proximal fractional reabsorption of sodium, the ability to reduce distal fractional reabsorption of sodium, the ability to increase urinary potassium excretion, the ability to reduce mean arterial pressure, the ability to reduce pulmonary capillary wedge pressure, the ability to reduce right atrial pressure, the ability to reduce pulmonary arterial pressure, the ability to reduce systemic vascular resistance, the ability to change pulmonary vascular resistance, the ability to increase hematocrit, the ability to reduce plasma renin activity, the ability to reduce plasma angiotensin II levels, the ability to reduce plasma aldosterone levels, the ability to increase plasma ANP immunoreactivity levels, the ability to increase urinary excretion of ANP, the ability to increase plasma CNP immunoreactivity levels, and the ability to increase urinary CNP excretion. In some cases, a polypeptide provided herein can exert mild effects on blood pressure. In some cases, a polypeptide provided herein can be an agonist for natriuretic peptide receptor-A, natriuretic peptide receptor-B, or both natriuretic peptide receptor-A and natriuretic peptide receptor-B.

In general, one aspect of this document features a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can lack the ability to induce excessive hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide.

In another aspect, this document features a polypeptide less than 44 amino acid residues in length, wherein the polypeptide comprises, in an order from amino terminus to carboxy terminus: (a) the sequence set forth in SEQ ID NO:6 or the sequence set forth in SEQ ID NO:6 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:7 or the sequence set forth in SEQ ID NO:7 with no more than three additions, subtractions, or substitutions. The polypeptide can comprise natriuretic activity. The polypeptide can comprise a cGMP-activating property. The polypeptide can comprise a natriuretic and diuretic activity. The polypeptide can comprise a cardiac-unloading activity. The polypeptide can lack the ability to induce excessive hypotension. The polypeptide can comprise the sequence set forth in SEQ ID NO:6. The polypeptide can comprise the sequence set forth in SEQ ID NO:2. The polypeptide can comprise the sequence set forth in SEQ ID NO:7. The polypeptide can comprise the sequence set forth in SEQ ID NO:6, the sequence set forth in SEQ ID NO:2, and the sequence set forth in SEQ ID NO:7. The polypeptide can comprise the sequence set forth in SEQ ID NO:6 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:7 with no more than three conservative amino acid substitutions. The polypeptide can be a substantially pure polypeptide.

In another aspect, this document features an isolated nucleic acid encoding a polypeptide selected from the group consisting of: (1) a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, and (2) a polypeptide less than 44 amino acid residues in length, wherein the polypeptide comprises, in an order from amino terminus to carboxy terminus: (a) the sequence set forth in SEQ ID NO:6 or the sequence set forth in SEQ ID NO:6 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:7 or the sequence set forth in SEQ ID NO:7 with no more than three additions, subtractions, or substitutions.

In another aspect, this document features a vector comprising a nucleic acid encoding a polypeptide selected from the group consisting of: (1) a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, and (2) a polypeptide less than 44 amino acid residues in length, wherein the polypeptide comprises, in an order from amino terminus to carboxy terminus: (a) the sequence set forth in SEQ ID NO:6 or the sequence set forth in SEQ ID NO:6 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:7 or the sequence set forth in SEQ ID NO:7 with no more than three additions, subtractions, or substitutions.

In another aspect, this document features a host cell comprising a nucleic acid encoding a polypeptide selected from the group consisting of: (1) a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, and (2) a polypeptide less than 44 amino acid residues in length, wherein the polypeptide comprises, in an order from amino terminus to carboxy terminus: (a) the sequence set forth in SEQ ID NO:6 or the sequence set forth in SEQ ID NO:6 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:7 or the sequence set forth in SEQ ID NO:7 with no more than three additions, subtractions, or substitutions. The host cell can be a eukaryotic host cell.

In another aspect, this document features a pharmaceutical composition comprising a pharmaceutically acceptable carrier and a polypeptide selected from the group consisting of: (1) a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, and (2) a polypeptide less than 44 amino acid residues in length, wherein the polypeptide comprises, in an order from amino terminus to carboxy terminus: (a) the sequence set forth in SEQ ID NO:6 or the sequence set forth in SEQ ID NO:6 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:7 or the sequence set forth in SEQ ID NO:7 with no more than three additions, subtractions, or substitutions.

In another aspect, this document features a method for increasing natriuretic activity within a mammal without excessively lowering blood pressure. The method comprises administering, to the mammal, a polypeptide selected from the group consisting of: (1) a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, and (2) a polypeptide less than 44 amino acid residues in length, wherein the polypeptide comprises, in an order from amino terminus to carboxy terminus: (a) the sequence set forth in SEQ ID NO:6 or the sequence set forth in SEQ ID NO:6 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:7 or the sequence set forth in SEQ ID NO:7 with no more than three additions, subtractions, or substitutions.

In another aspect, this document features a method for treating a mammal having a cardiovascular condition or renal condition. The method comprises administering, to the mammal, a polypeptide under conditions wherein the severity of a manifestation of the cardiovascular condition or renal condition is reduced. The polypeptide is selected from the group consisting of: (1) a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions, and (2) a polypeptide less than 44 amino acid residues in length, wherein the polypeptide comprises, in an order from amino terminus to carboxy terminus: (a) the sequence set forth in SEQ ID NO:6 or the sequence set forth in SEQ ID NO:6 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:7 or the sequence set forth in SEQ ID NO:7 with no more than three additions, subtractions, or substitutions. Administration of the polypeptide to the mammal can be such that it does not excessively lower the blood pressure of the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is a schematic diagram of a BAA-NP polypeptide that is 28 amino acid residues in length (SEQ ID NO:4). The first six amino acid residues of SEQ ID NO:4 correspond to amino acid residues 1 to 6 of human ANP and are designated as SEQ ID NO:1. Amino acid residues 7 to 23 of SEQ ID NO:4 correspond to amino acid residues 10 to 26 of human mature BNP and are designated as SEQ ID NO:2. Amino acid residues 24 to 28 of SEQ ID NO:4 correspond to amino acid residues 24 to 28 of human ANP and are designated as SEQ ID NO:3.

FIG. 2 is a schematic diagram of a BUA-NP polypeptide that is 32 amino acid residues in length (SEQ ID NO:5). The first ten amino acid residues of SEQ ID NO:5 correspond to amino acid residues 1 to 10 of human urodilatin and are designated as SEQ ID NO:6. Amino acid residues 11 to 27 of SEQ ID NO:5 correspond to amino acid residues 10 to 26 of human mature BNP and are designated as SEQ ID NO:2. Amino acid residues 28 to 32 of SEQ ID NO:4 correspond to amino acid residues 27 to 32 of human ANP and are designated as SEQ ID NO:7.

DETAILED DESCRIPTION

Figure 3:
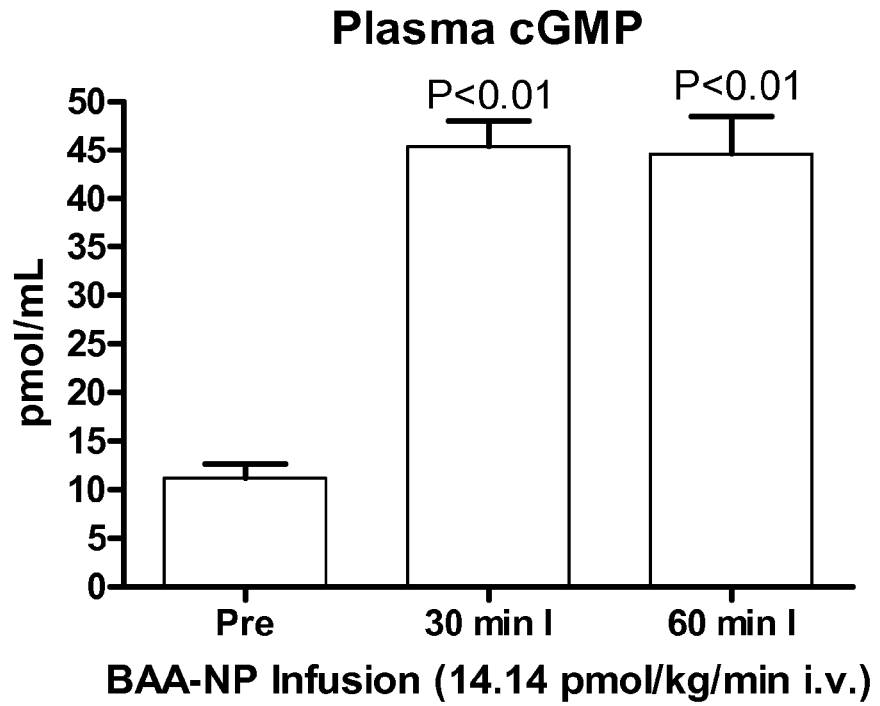
FIG. 3 is a graph plotting plasma cGMP levels before and during BAA-NP infusion (n=6).
Figure 4:
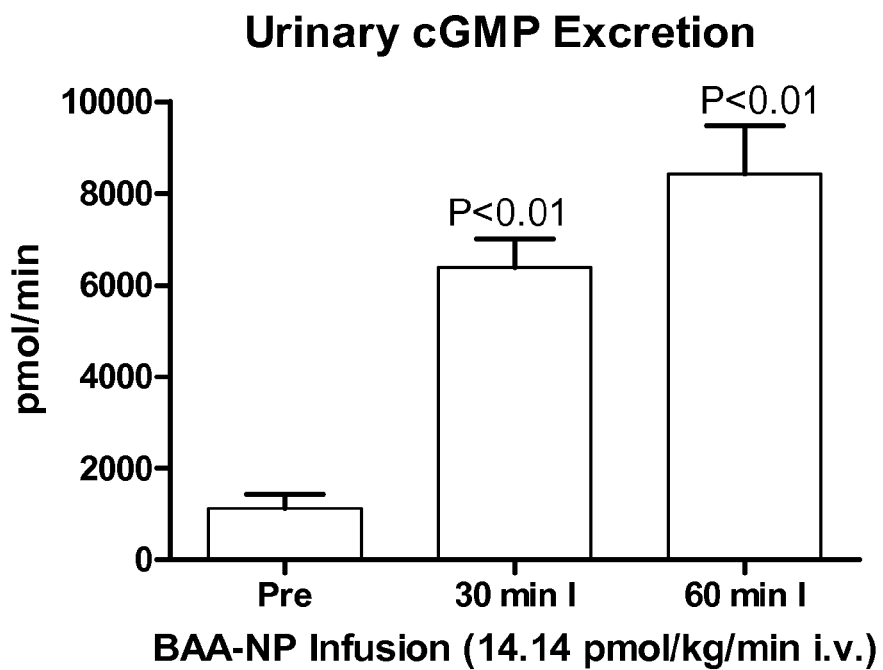
FIG. 4 is a graph plotting urinary cGMP excretion before and during BAA-NP infusion (n=6).
Figure 5:
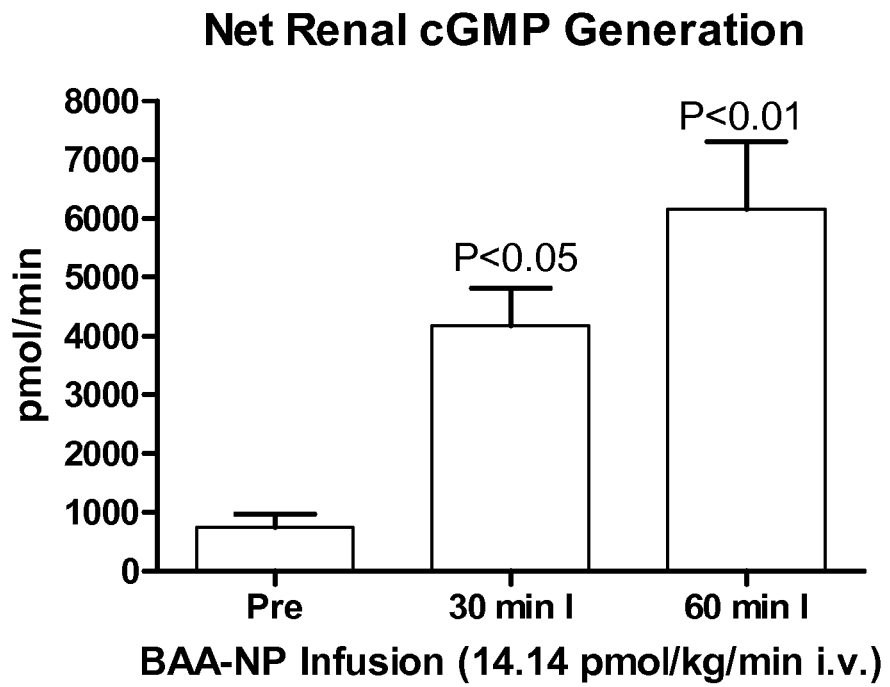
FIG. 5 is a graph plotting net renal generation of cGMP before and during BAA-NP infusion (n=5).
Figure 6:
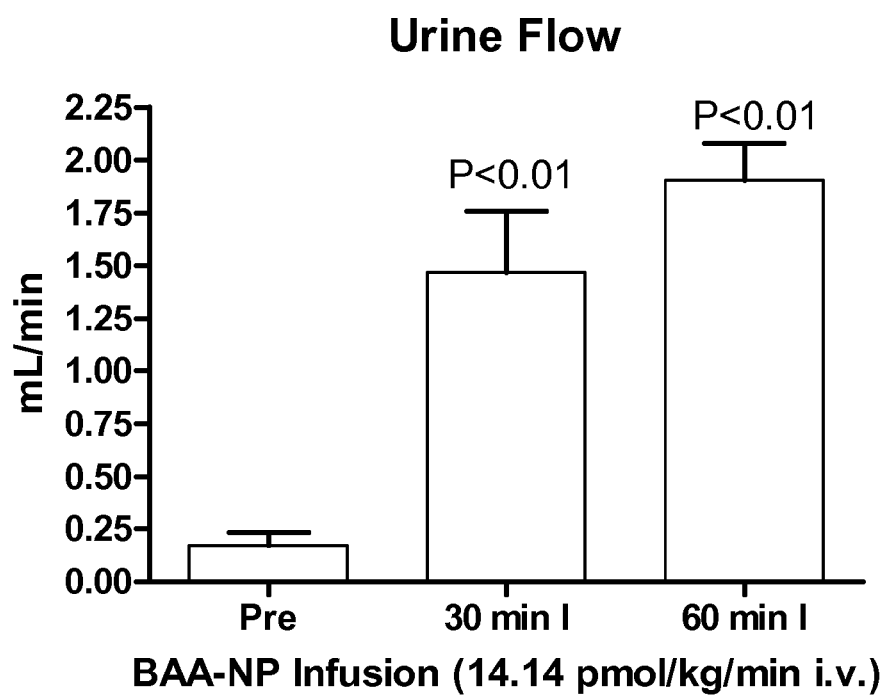
FIG. 6 is a graph plotting urine flow before and during BAA-NP infusion (n=6).
Figure 7:
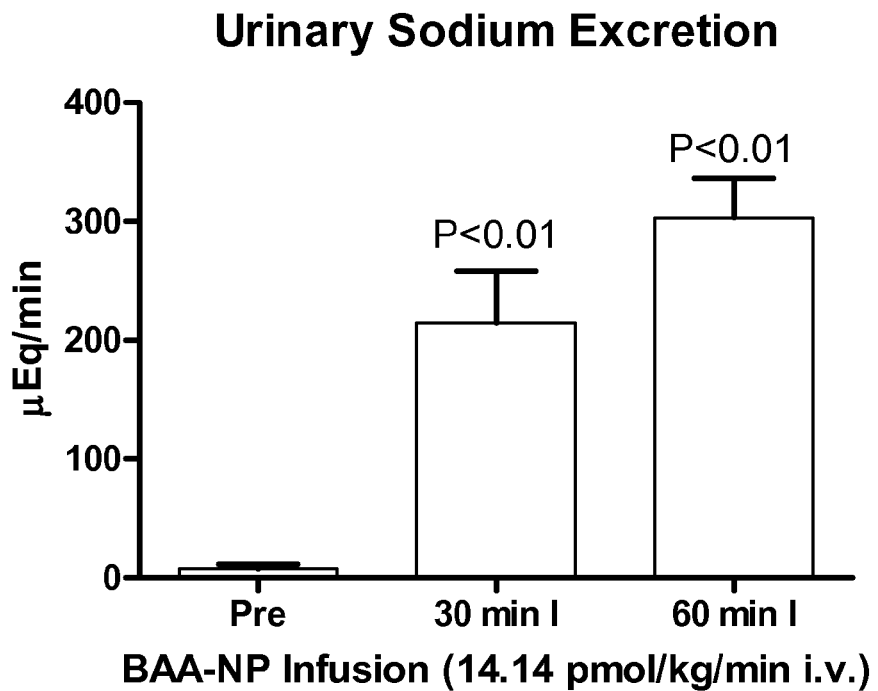
FIG. 7 is a graph plotting urinary sodium excretion before and during BAA-NP infusion (n=6).
Figure 8:
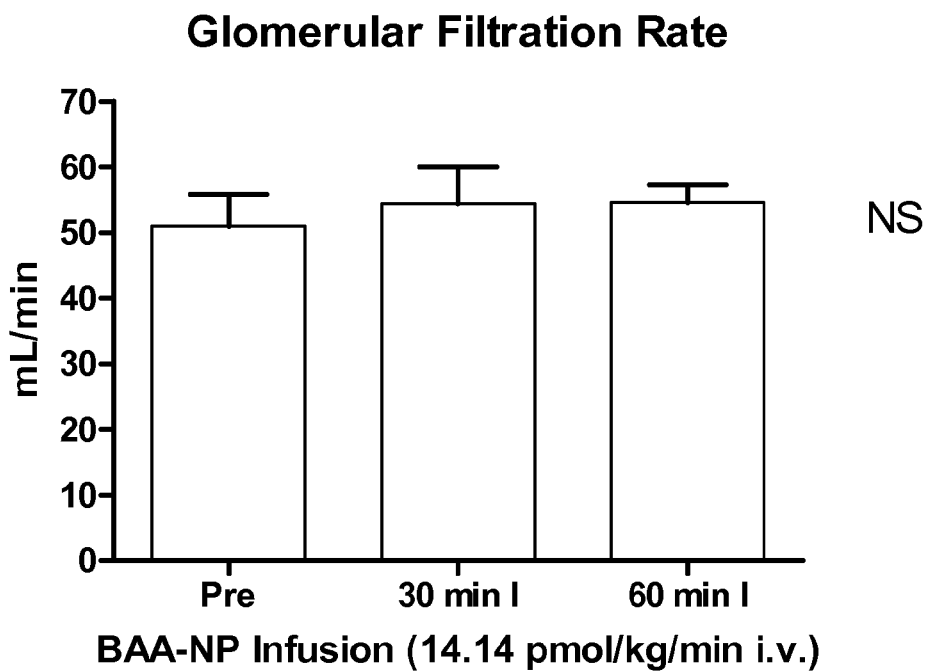
FIG. 8 is a graph plotting glomerular filtration rate before and during BAA-NP infusion (n=6).
Figure 9:
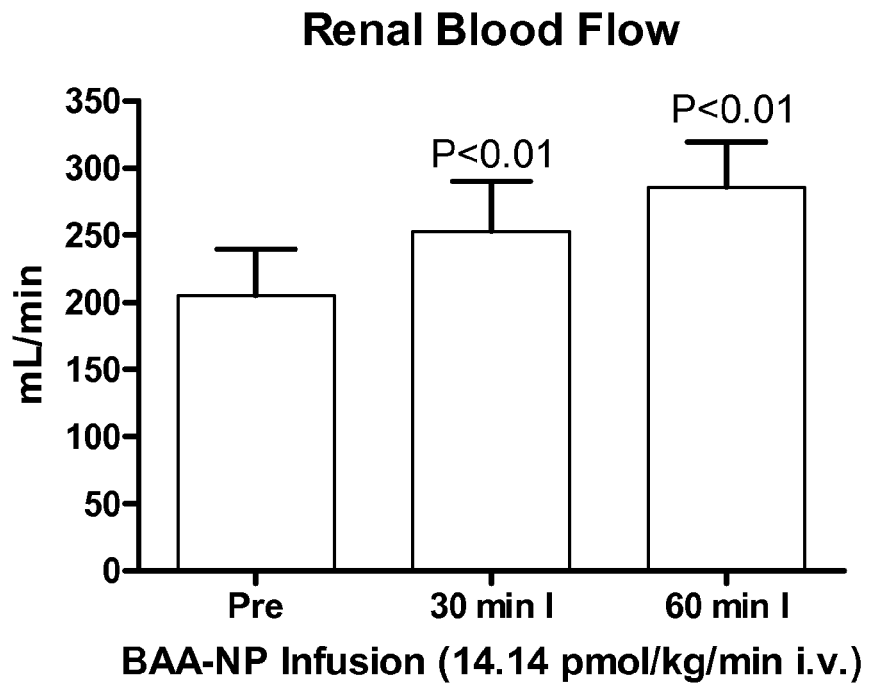
FIG. 9 is a graph plotting renal blood flow before and during BAA-NP infusion (n=6).
Figure 10:
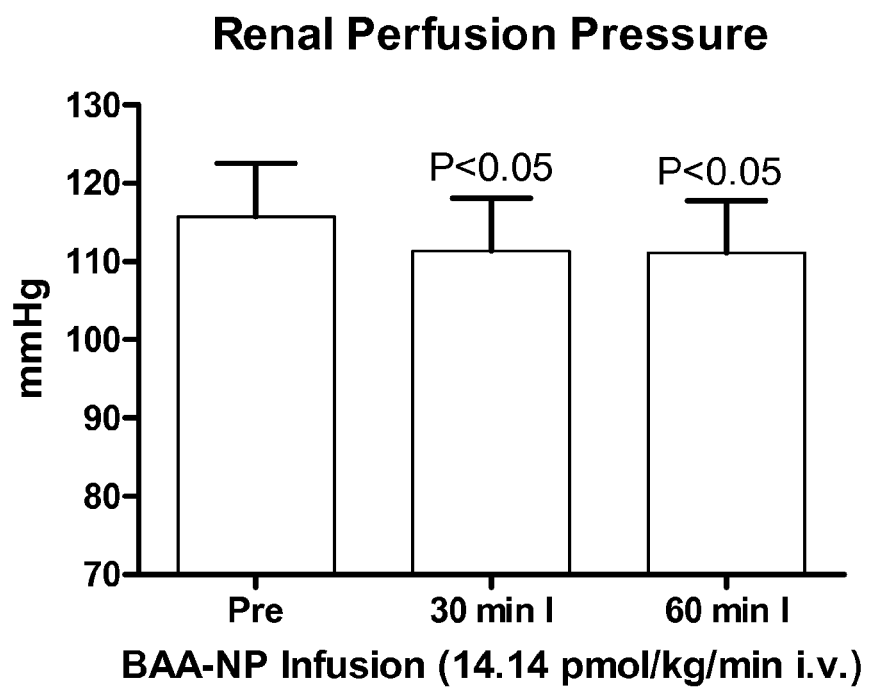
FIG. 10 is a graph plotting renal perfusion pressure before and during BAA-NP infusion (n=6).
Figure 11:
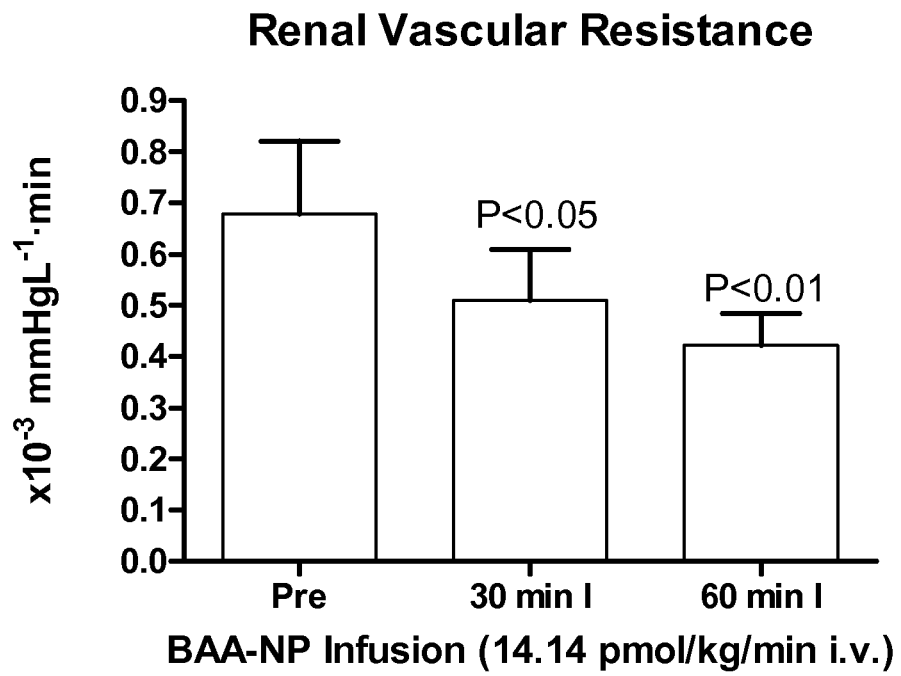
FIG. 11 is a graph plotting renal vascular resistance before and during BAA-NP infusion (n=6).
Figure 12:
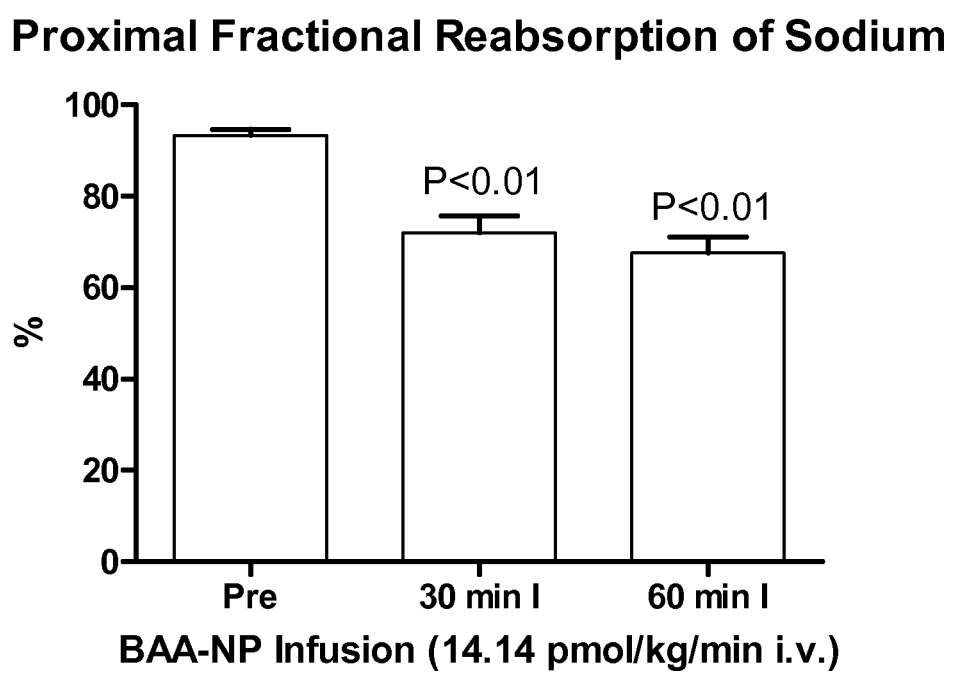
FIG. 12 is a graph plotting proximal fractional reabsorption of sodium before and during BAA-NP infusion (n=4).
Figure 13:
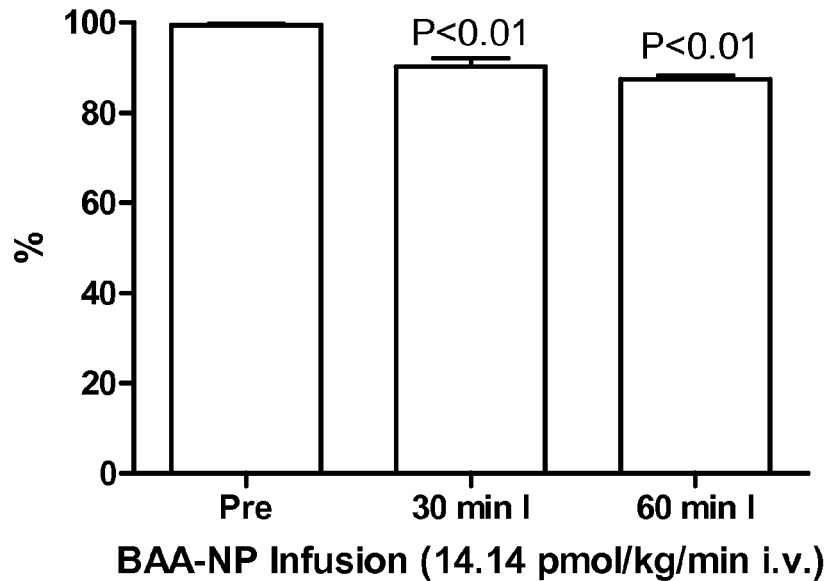
FIG. 13 is a graph plotting distal fractional reabsorption of sodium before and during BAA-NP infusion (n=4).
Figure 14:
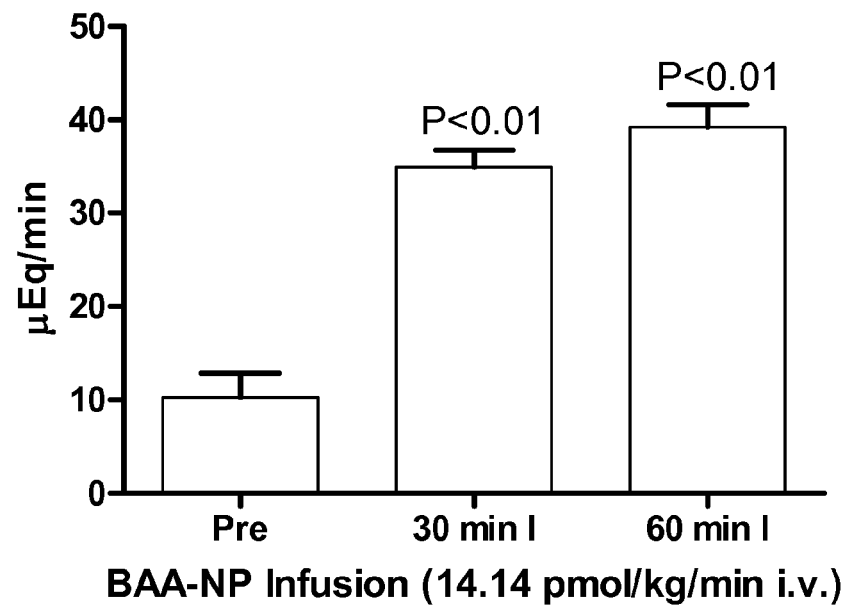
FIG. 14 is a graph plotting urinary potassium excretion before and during BAA-NP infusion (n=6).
Figure 15:
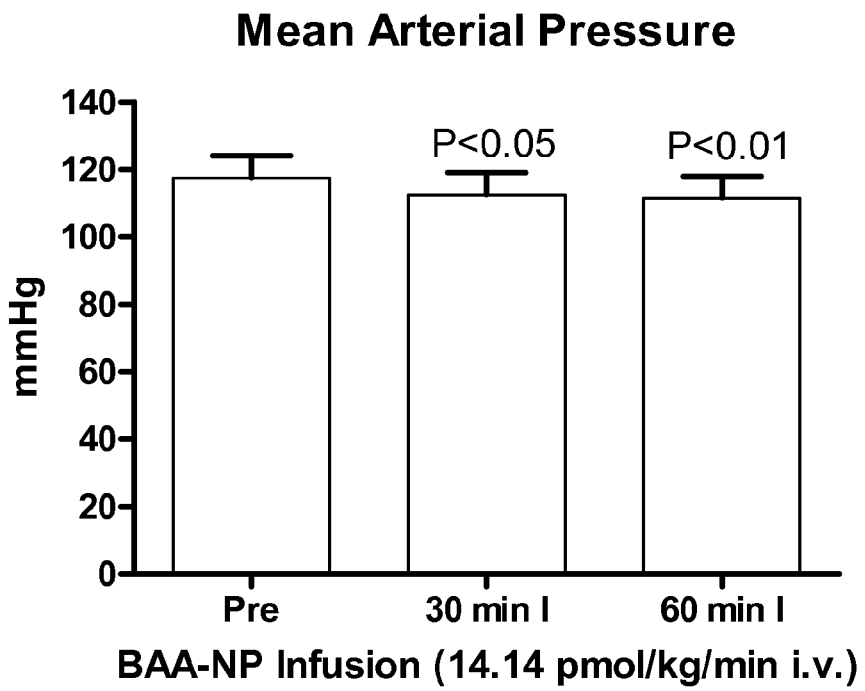
FIG. 15 is a graph plotting mean arterial pressure before and during BAA-NP infusion (n=6).
Figure 16:
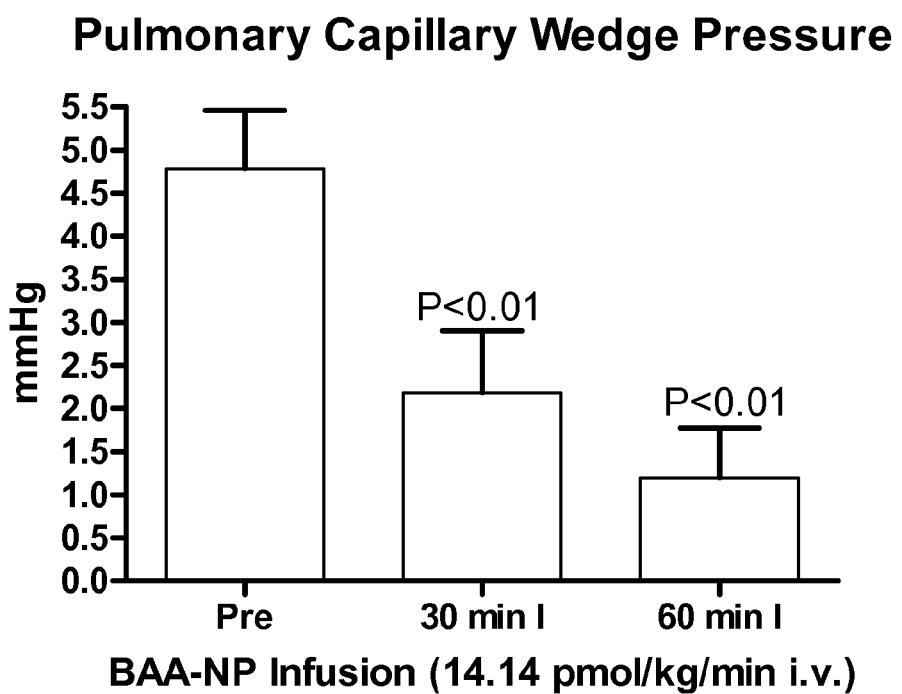
FIG. 16 is a graph plotting pulmonary capillary wedge pressure before and during BAA-NP infusion (n=6).
Figure 17:
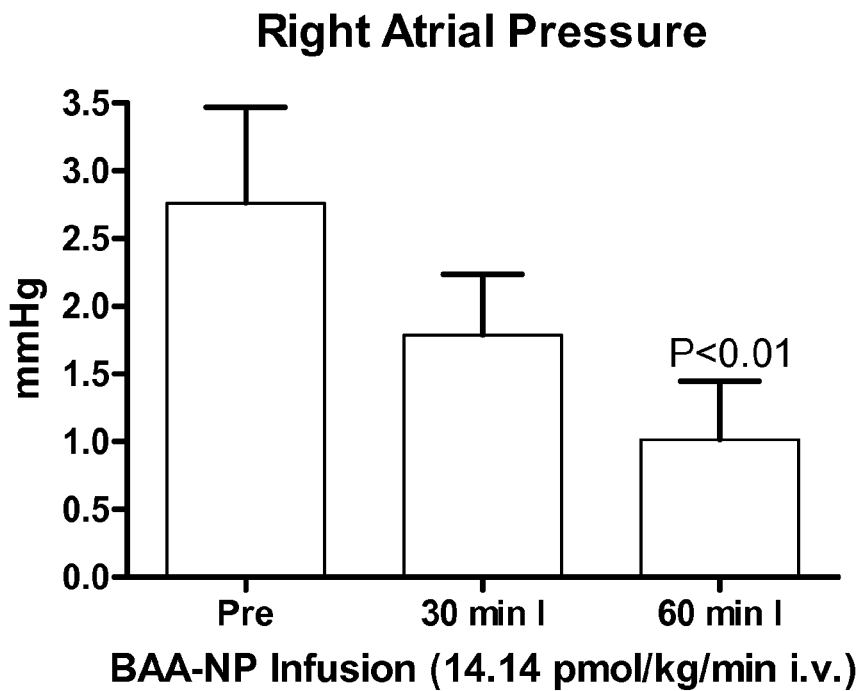
FIG. 17 is a graph plotting right atrial pressure before and during BAA-NP infusion (n=6).
Figure 18:
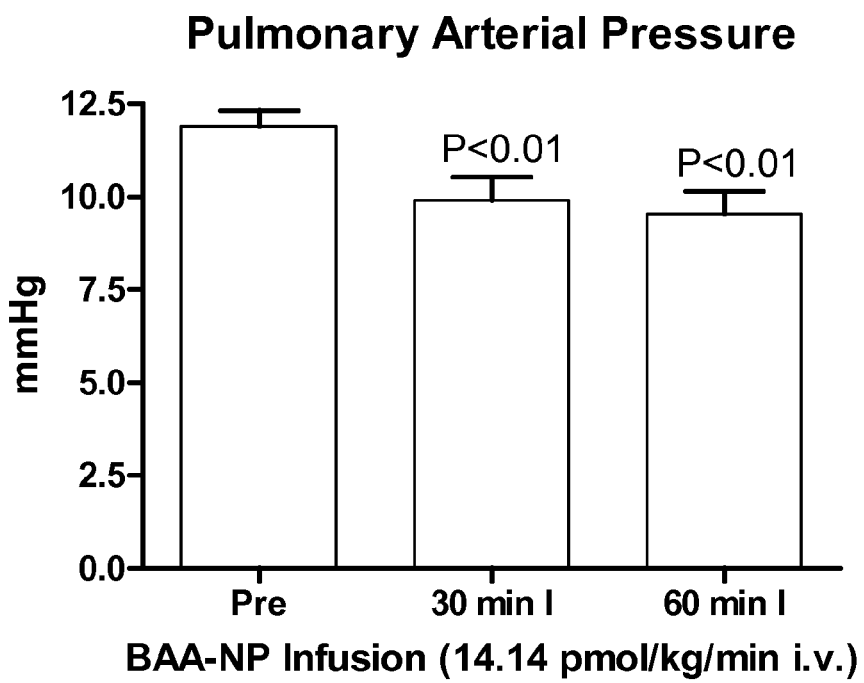
FIG. 18 is a graph plotting pulmonary arterial pressure before and during BAA-NP infusion (n=6).
Figure 19:
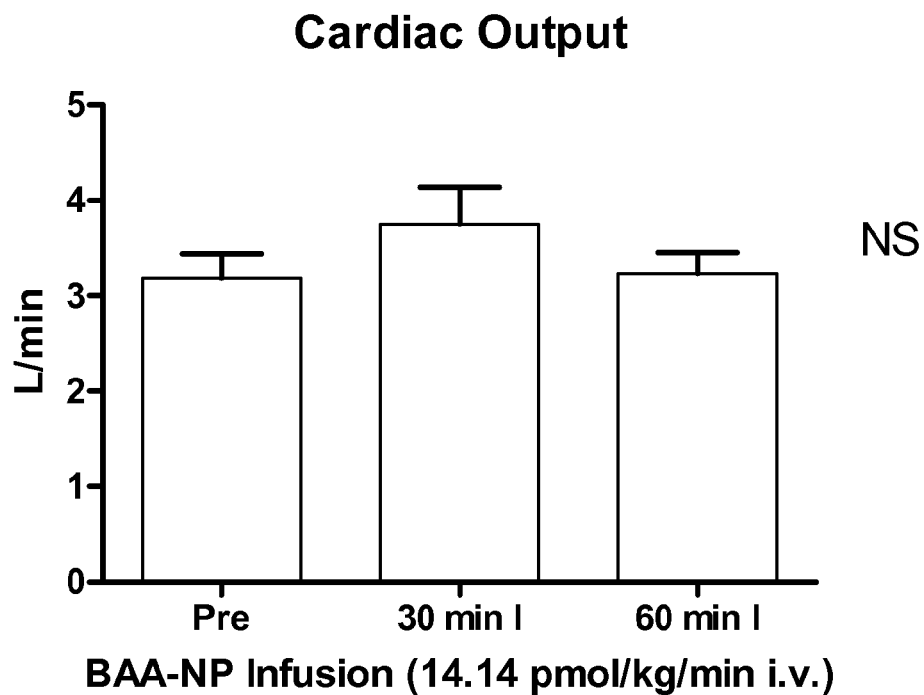
FIG. 19 is a graph plotting cardiac output before and during BAA-NP infusion (n=6).
Figure 20:
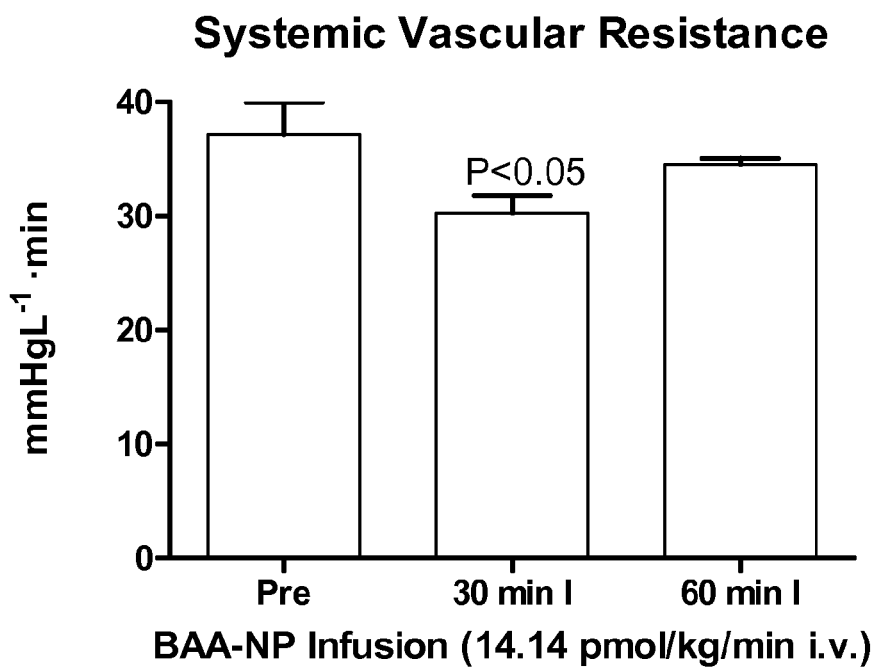
FIG. 20 is a graph plotting systemic vascular resistance before and during BAA-NP infusion (n=6).
Figure 21:
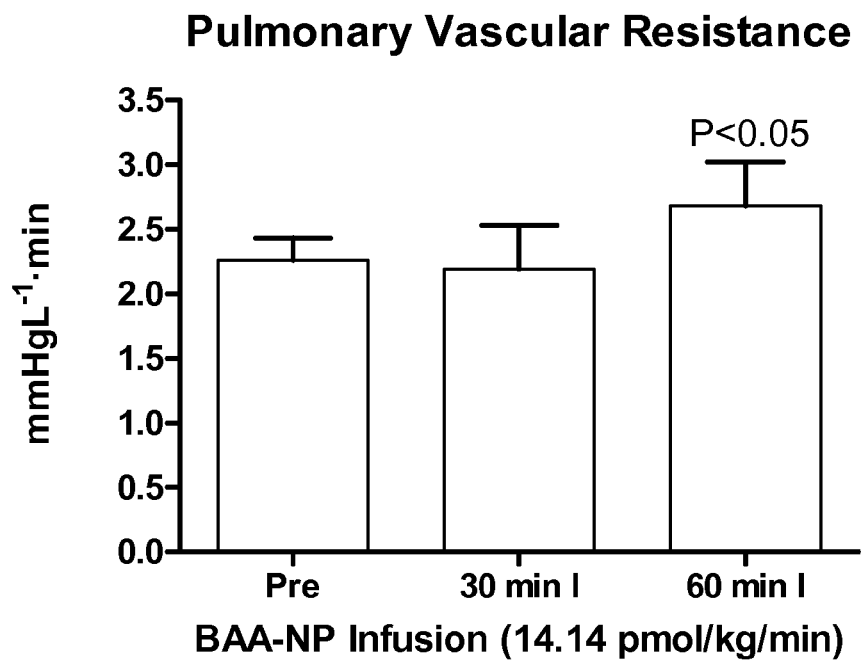
FIG. 21 is a graph plotting pulmonary vascular resistance before and during BAA-NP infusion (n=6).
Figure 22:
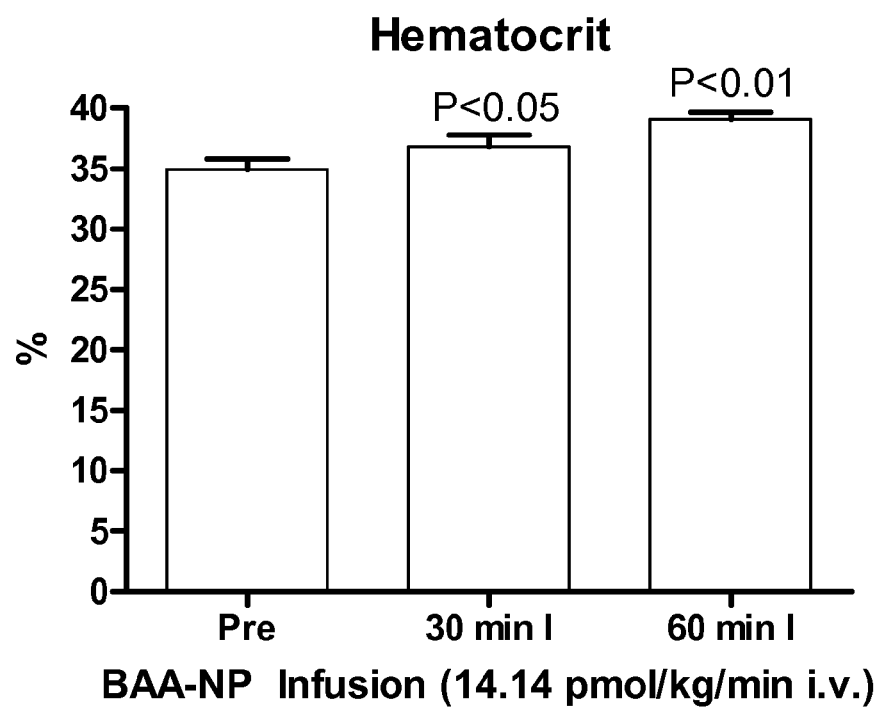
FIG. 22 is a graph plotting hematocrit levels before and during BAA-NP infusion (n=6).
Figure 23:
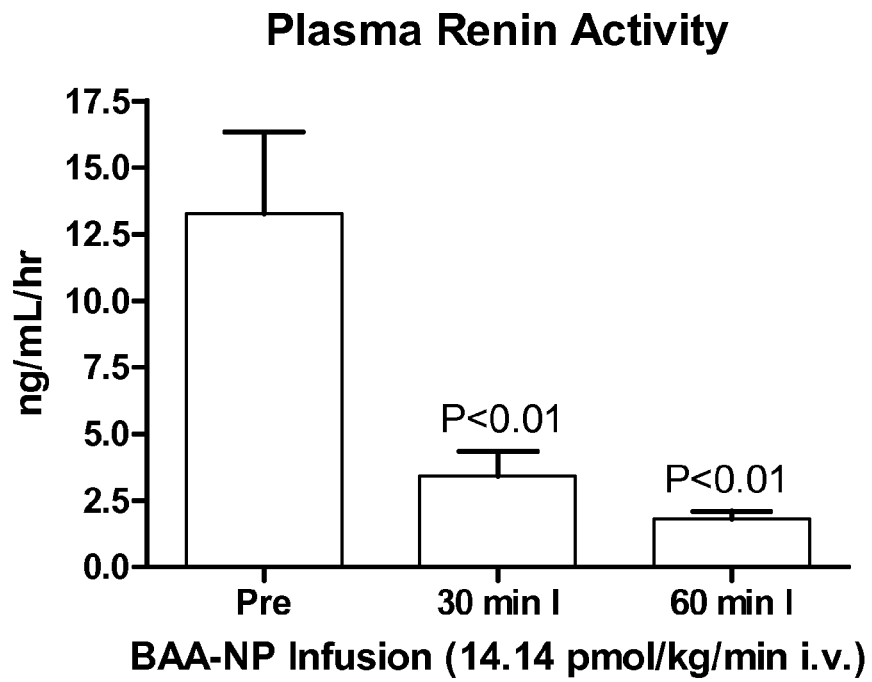
FIG. 23 is a graph plotting plasma renin activity before and during BAA-NP infusion (n=6).
Figure 24:
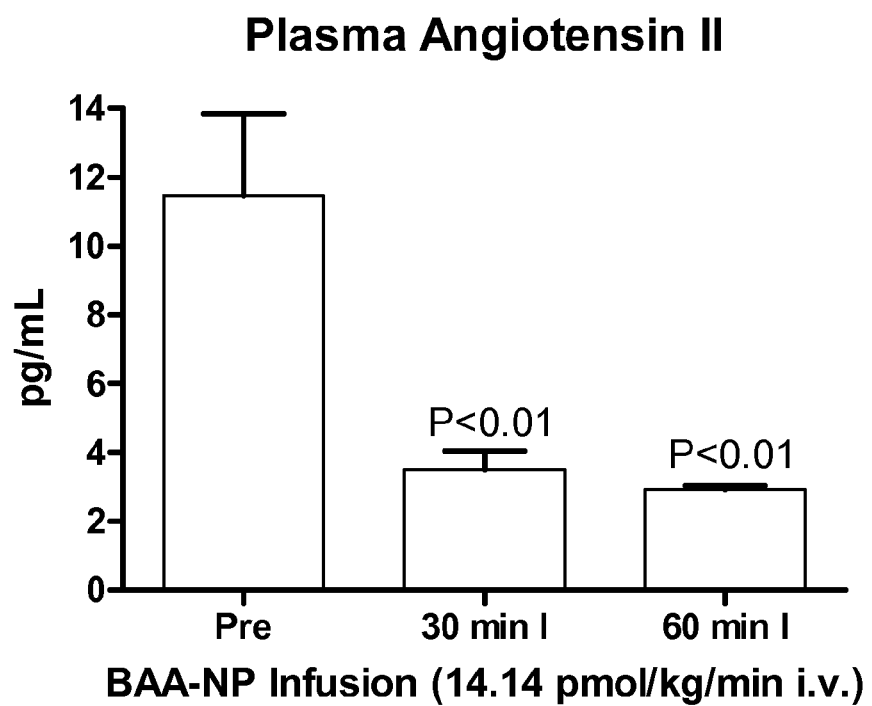
FIG. 24 is a graph plotting plasma angiotensin ii before and during BAA-NP infusion (n=6).
Figure 25:
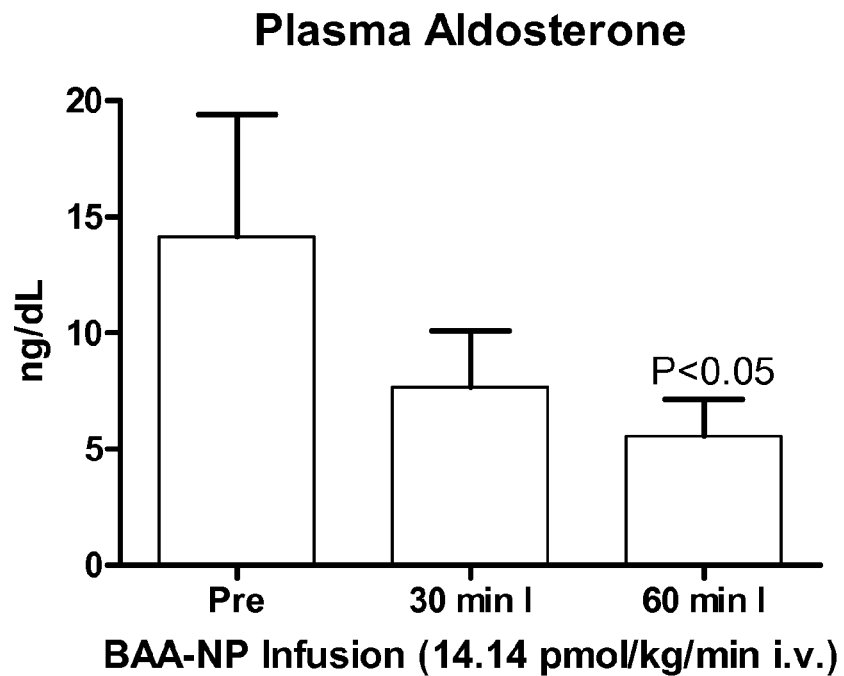
FIG. 25 is a graph plotting plasma aldosterone before and during BAA-NP infusion (n=5).
Figure 26:
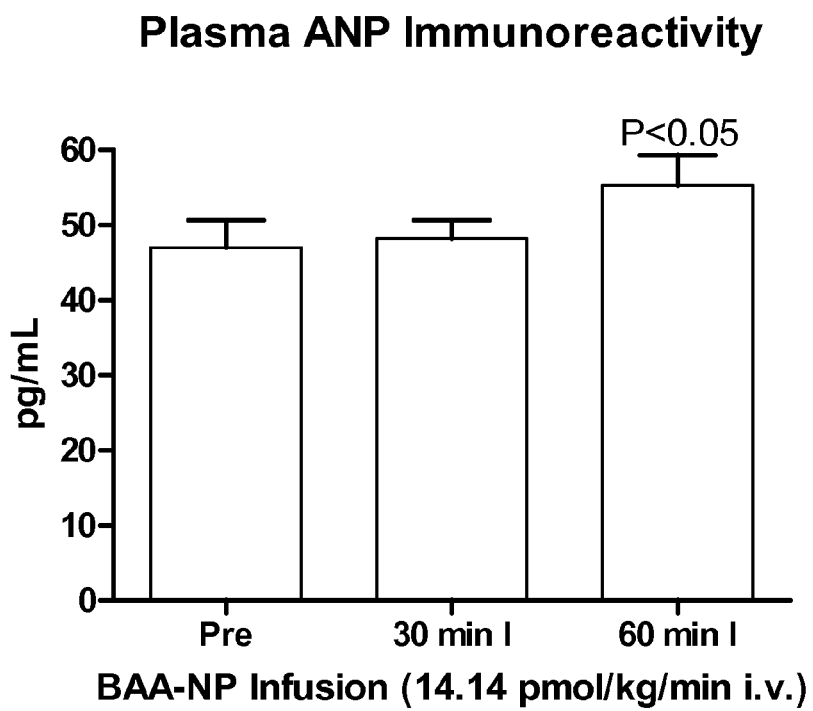
FIG. 26 is a graph plotting plasma ANP immunoreactivity before and during BAA-NP infusion (n=6).
Figure 27:
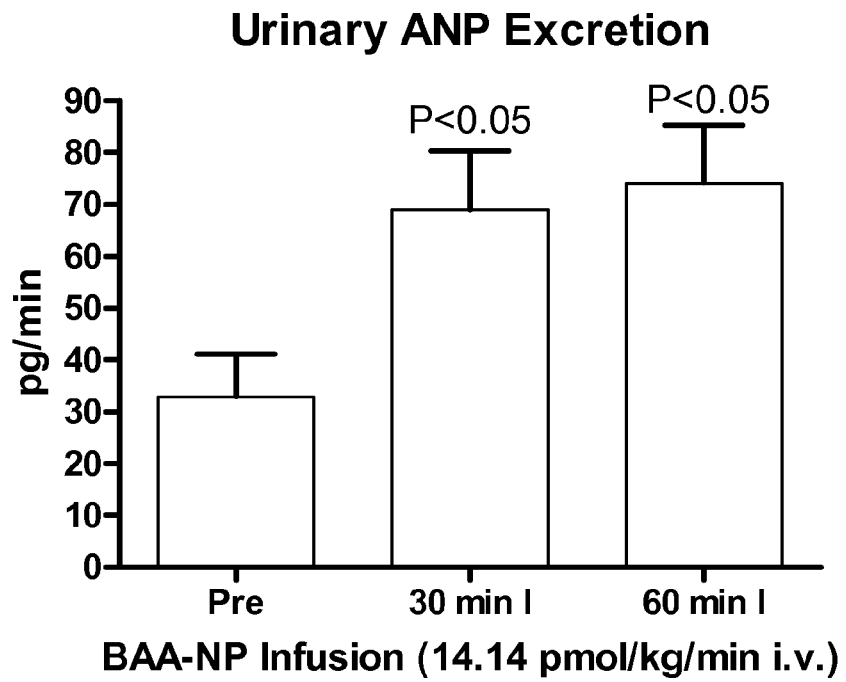
FIG. 27 is a graph plotting urinary excretion of ANP before and during BAA-NP infusion (n=6).
Figure 28:
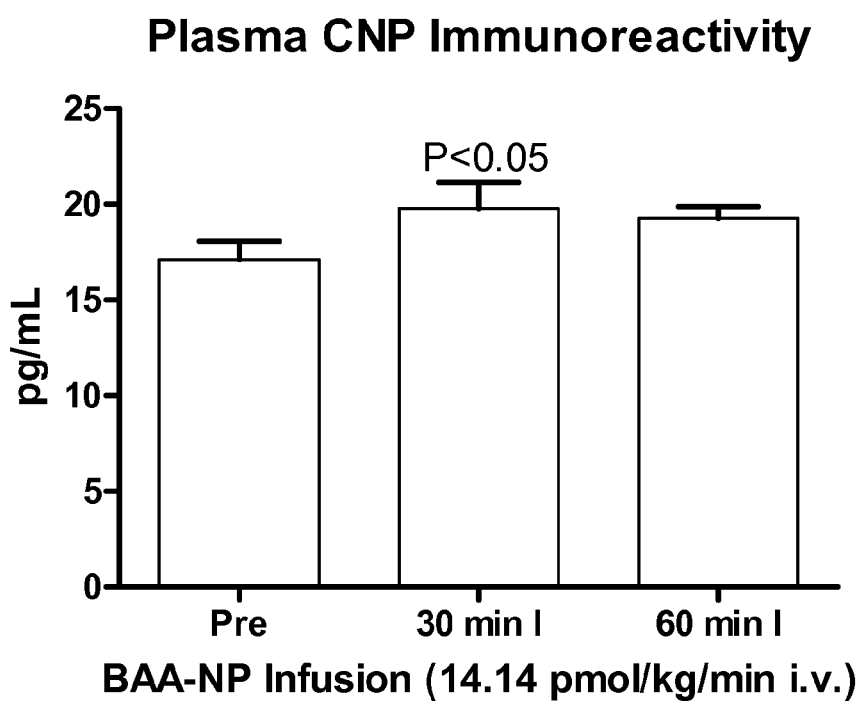
FIG. 28 is a graph plotting plasma CNP immunoreactivity before and during BAA-NP infusion (n=6).
Figure 29:
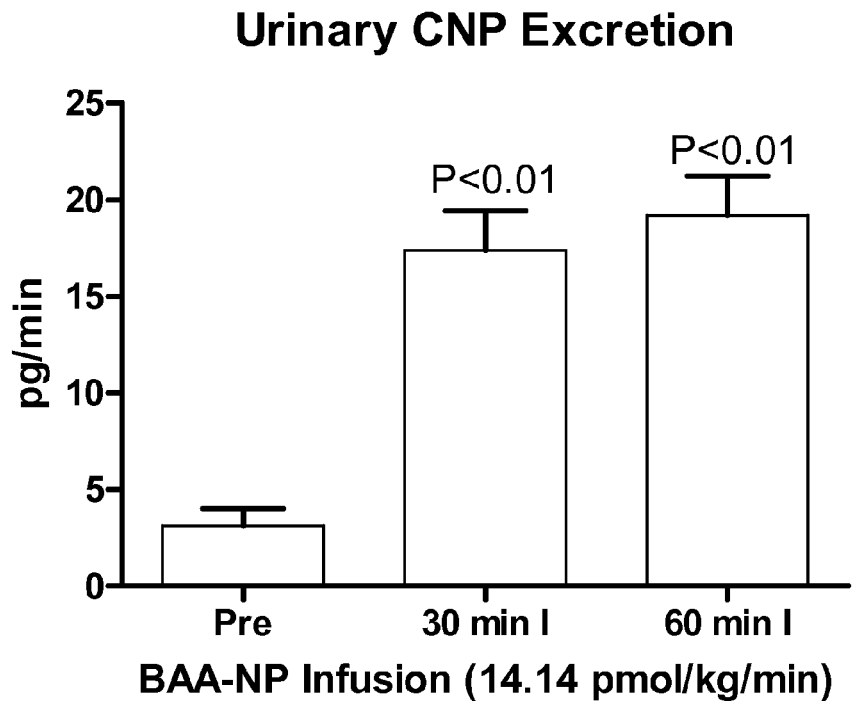
FIG. 29 is a graph plotting urinary CNP excretion before and during BAA-NP infusion (n=5).
Figure 30:
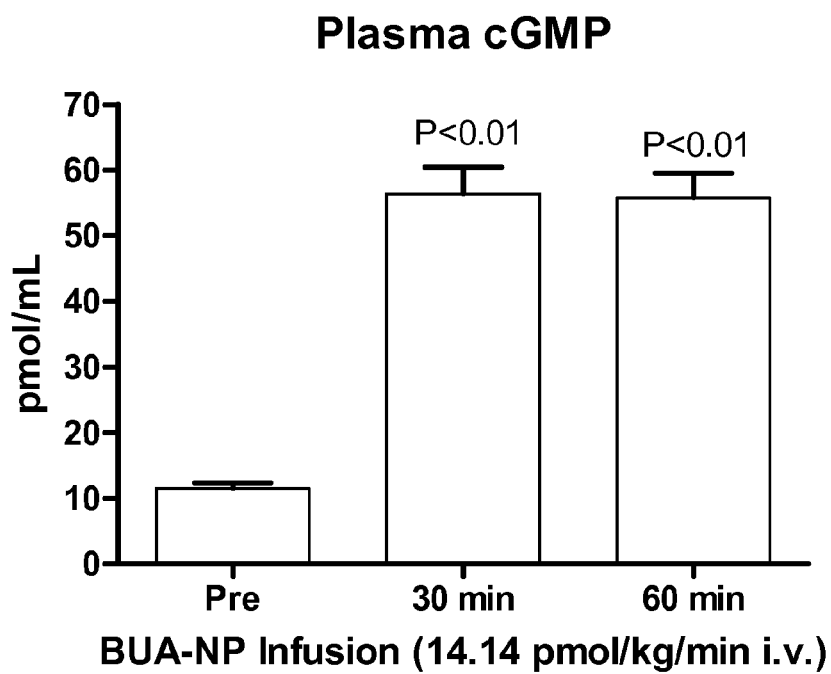
FIG. 30 is a graph plotting plasma cGMP before and during BUA-NP infusion (n=6).
Figure 31:
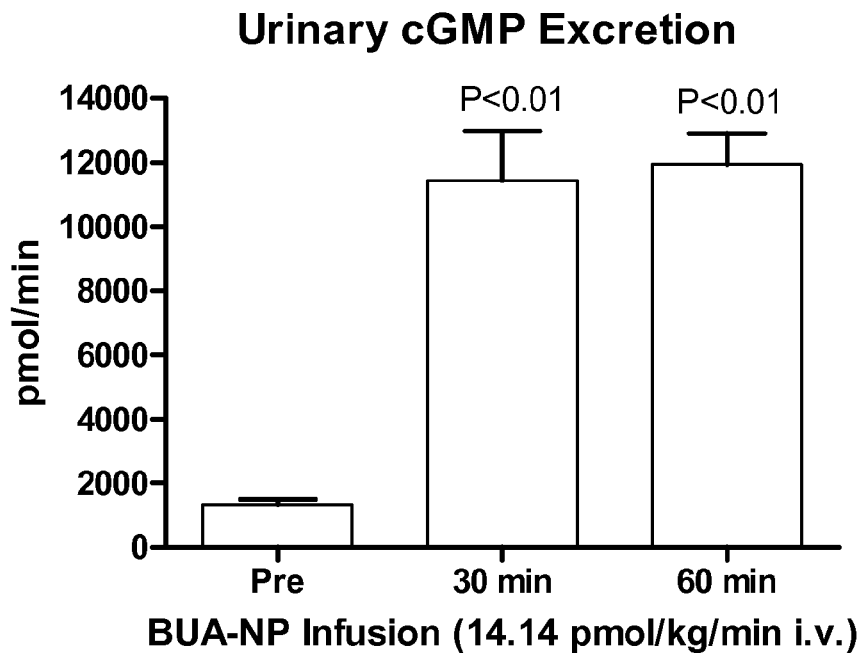
FIG. 31 is a graph plotting urinary cGMP excretion before and during BUA-NP infusion (n=6).
Figure 32:
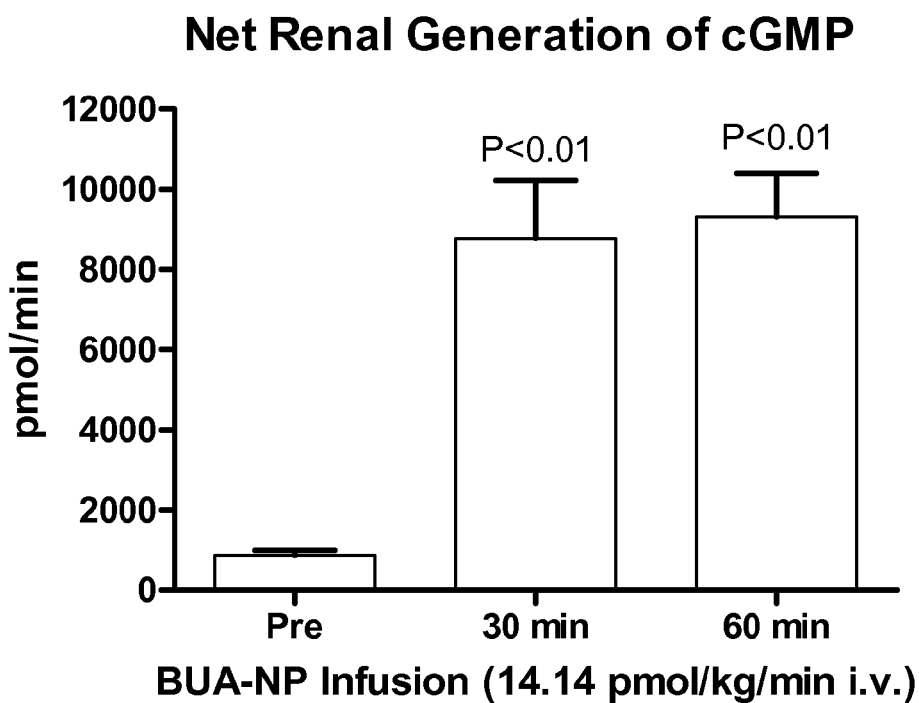
FIG. 32 is a graph plotting net renal generation of cGMP before and during BUA-NP infusion (n=6).
Figure 33:
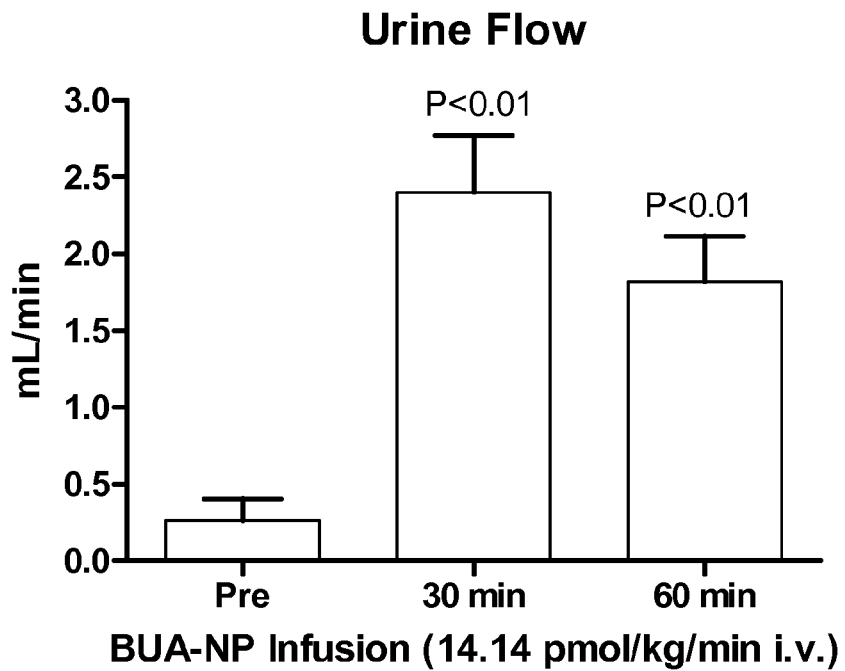
FIG. 33 is a graph plotting urine flow before and during BUA-NP infusion (n=6).
Figure 34:
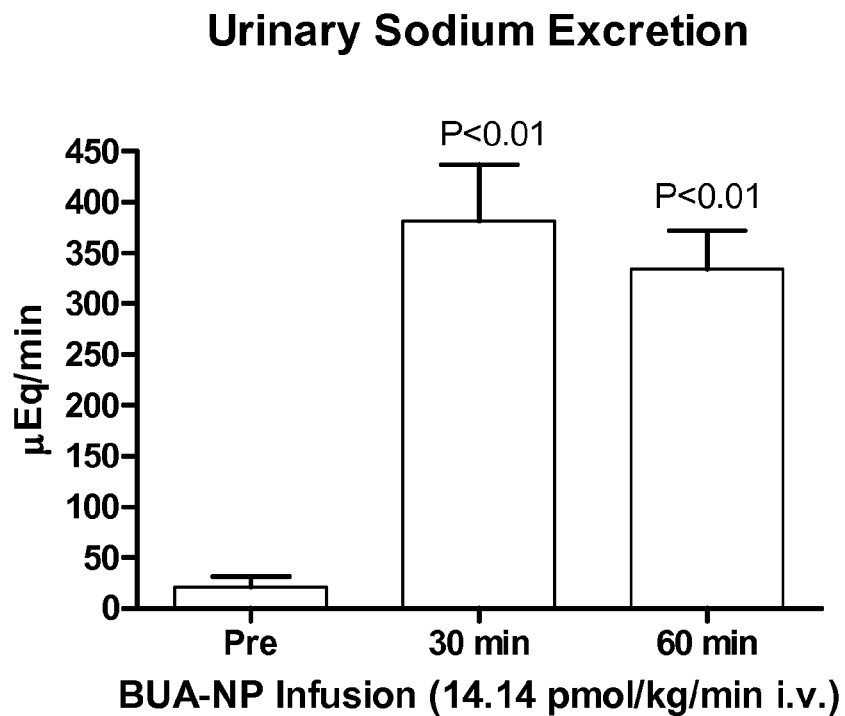
FIG. 34 is a graph plotting urinary sodium excretion before and during BUA-NP infusion (n=6).
Figure 35:
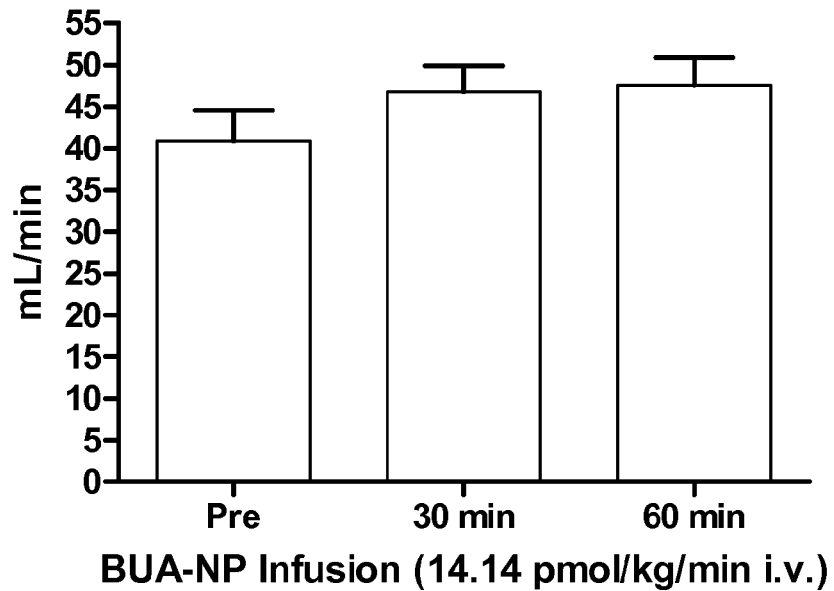
FIG. 35 is a graph plotting glomerular filtration rate before and during BUA-NP infusion (n=6).
Figure 36:
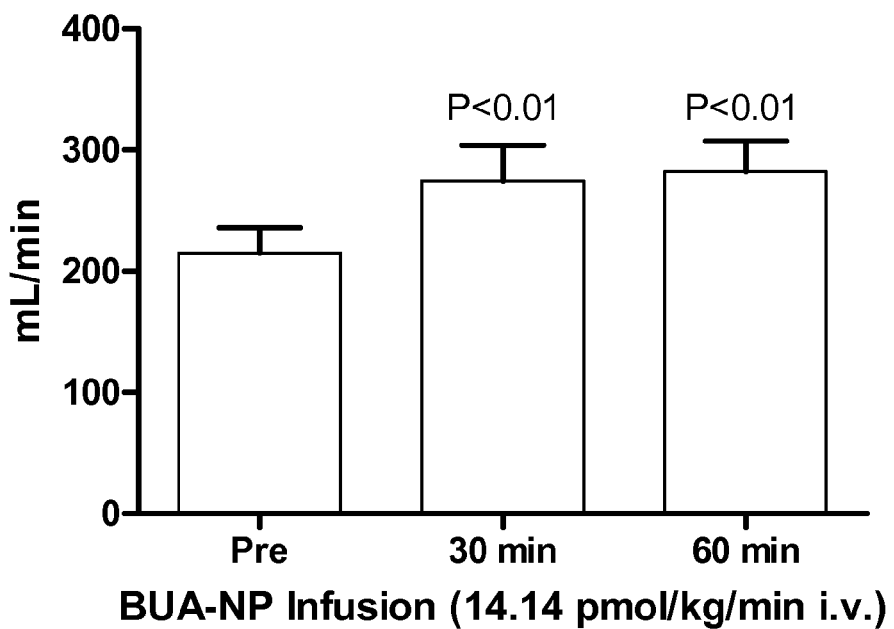
FIG. 36 is a graph plotting renal blood flow before and during BUA-NP infusion (n=6).
Figure 37:
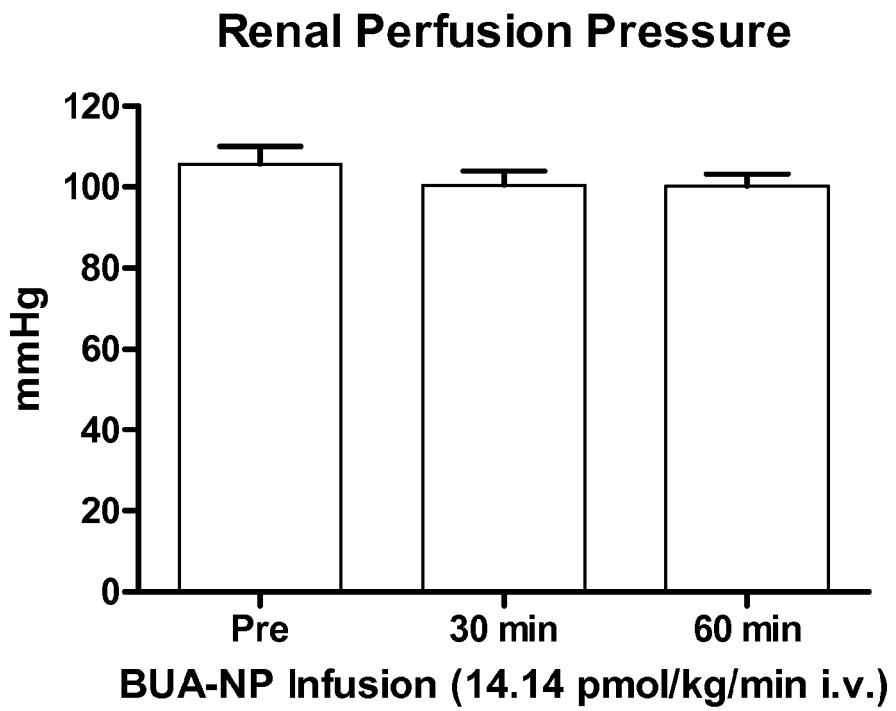
FIG. 37 is a graph plotting renal perfusion pressure before and during BUA-NP infusion (n=6).
Figure 38:
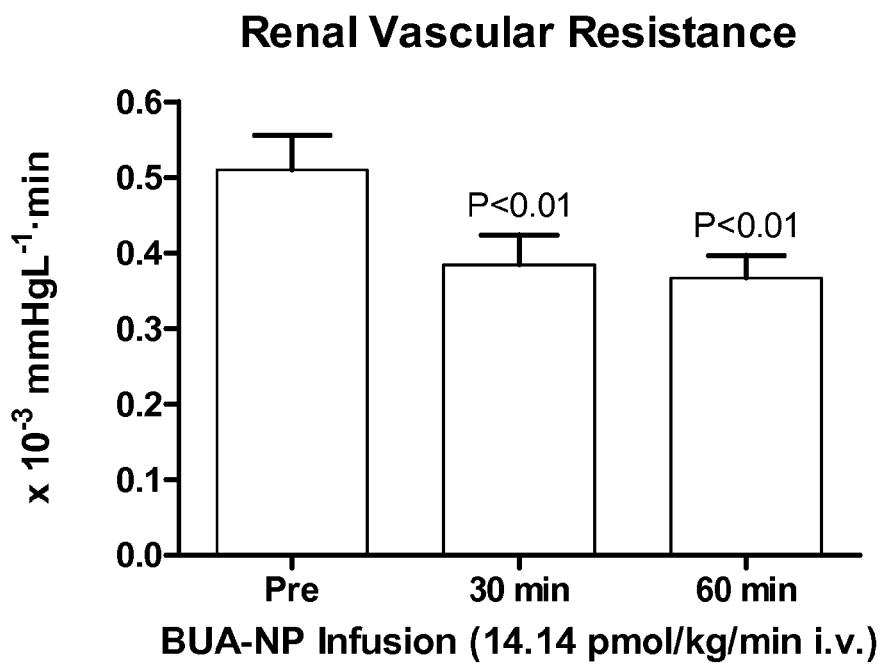
FIG. 38 is a graph plotting renal vascular resistance before and during BUA-NP infusion (n=6).
Figure 39:
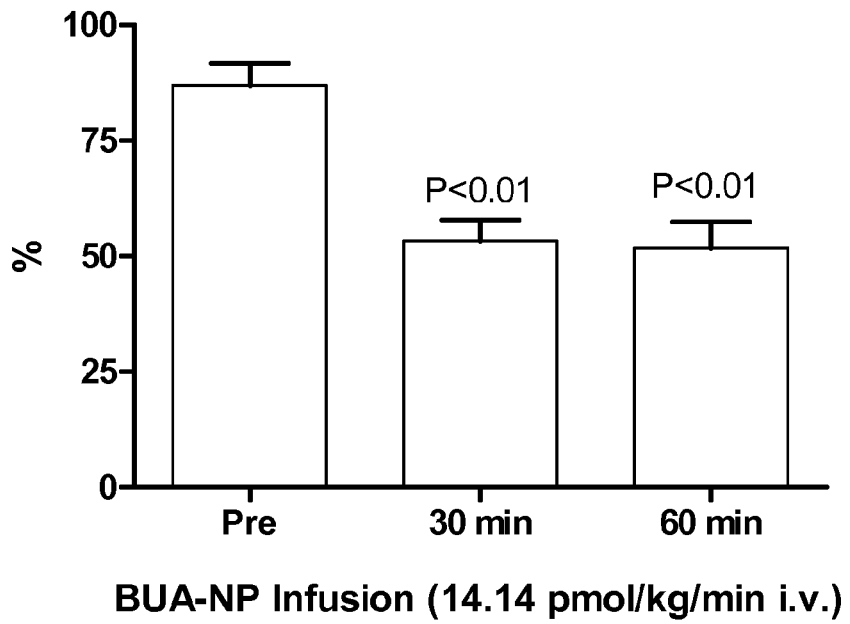
FIG. 39 is a graph plotting proximal fractional reabsorption of sodium before and during BUA-NP infusion (n=4).
Figure 40:
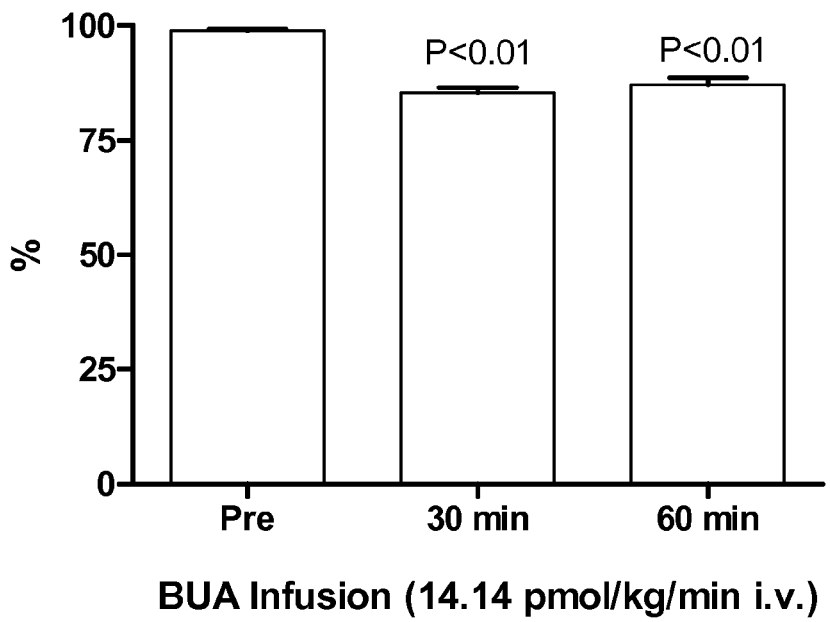
FIG. 40 is a graph plotting distal fractional reabsorption of sodium before and during BUA-NP infusion (n=4).
Figure 41:
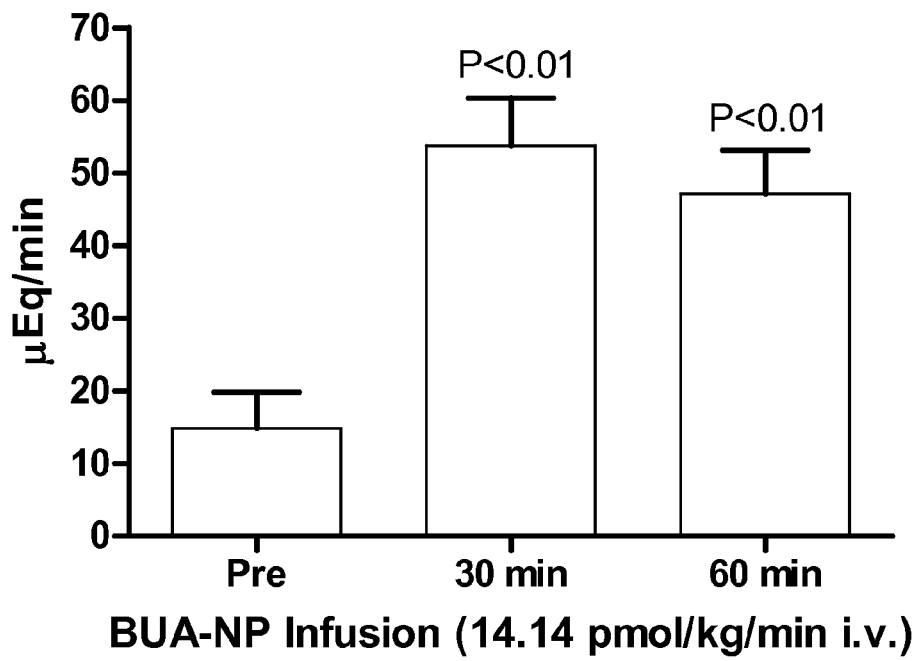
FIG. 41 is a graph plotting urinary potassium excretion before and during BUA-NP infusion (n=6).
Figure 42:
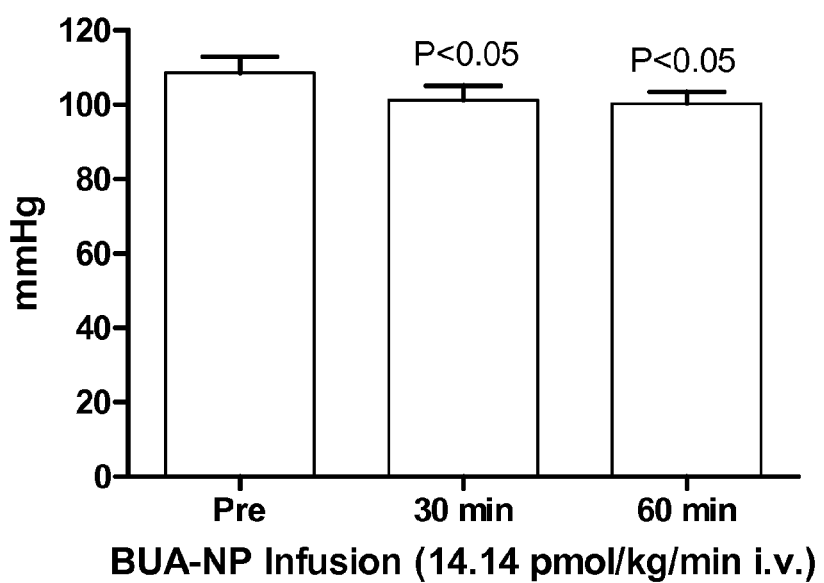
FIG. 42 is a graph plotting mean arterial pressure before and during BUA-NP infusion (n=6).
Figure 43:
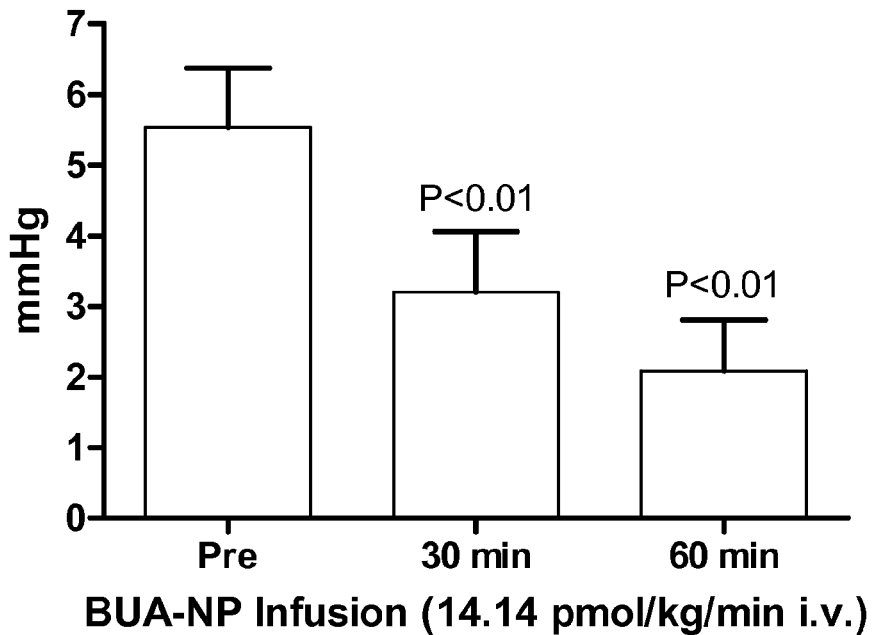
FIG. 43 is a graph plotting pulmonary capillary wedge pressure before and during BUA-NP infusion (n=6).
Figure 44:
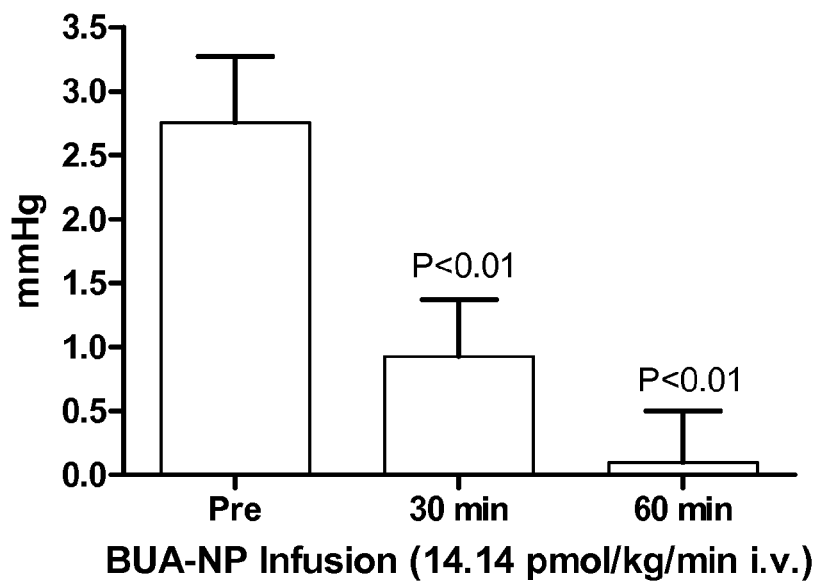
FIG. 44 is a graph plotting right atrial pressure before and during BUA-NP infusion (n=6).
Figure 45:
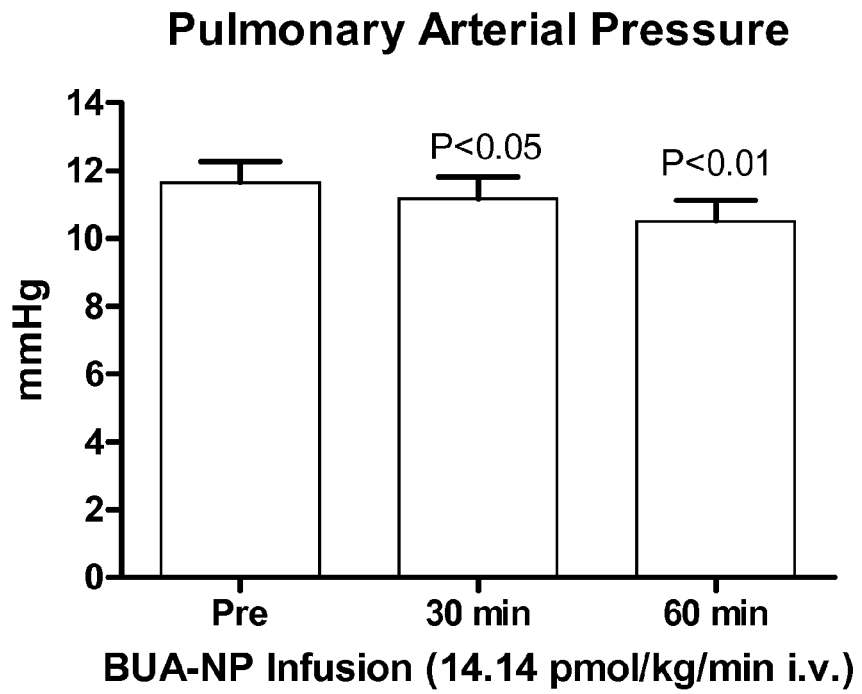
FIG. 45 is a graph plotting pulmonary arterial pressure before and during BUA-NP infusion (n=6).
Figure 46:
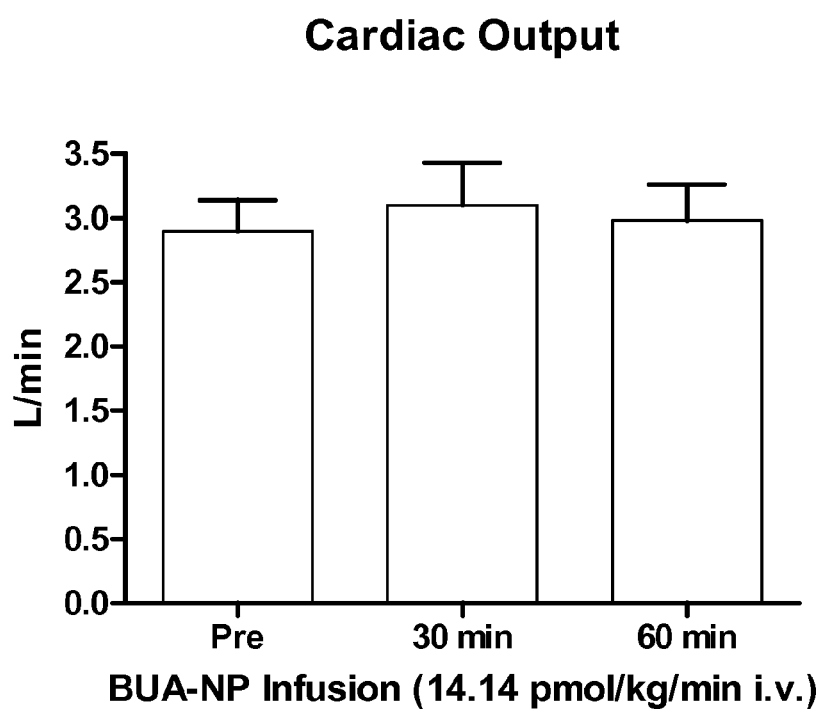
FIG. 46 is a graph plotting cardiac output before and during BUA-NP infusion (n=6).
Figure 47:
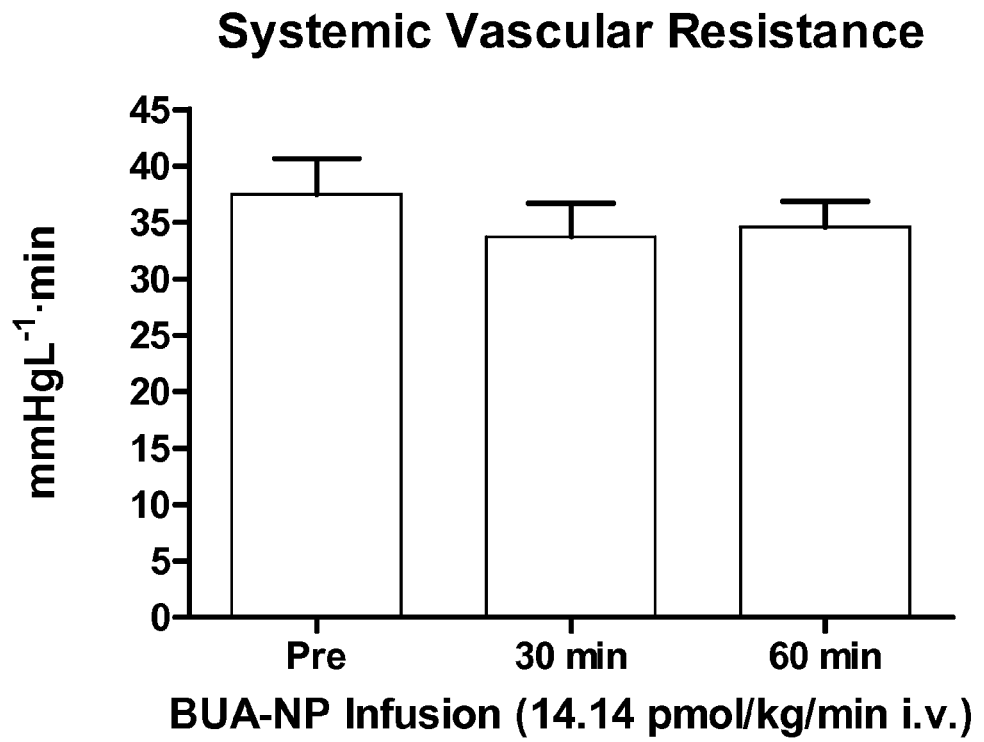
FIG. 47 is a graph plotting systemic vascular resistance before and during BUA-NP infusion (n=6).
Figure 48:
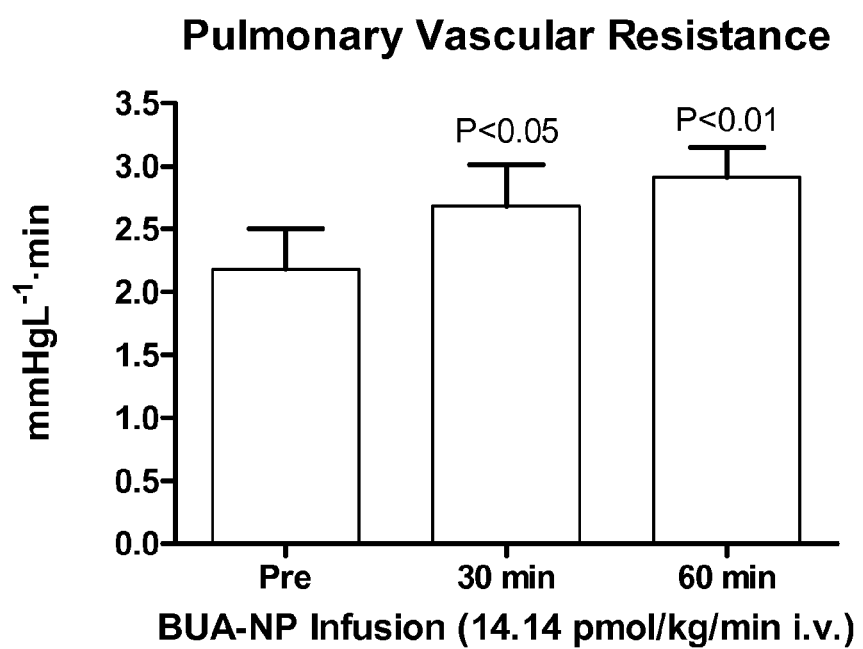
FIG. 48 is a graph plotting pulmonary vascular resistance before and during BUA-NP infusion (n=6).
Figure 49:
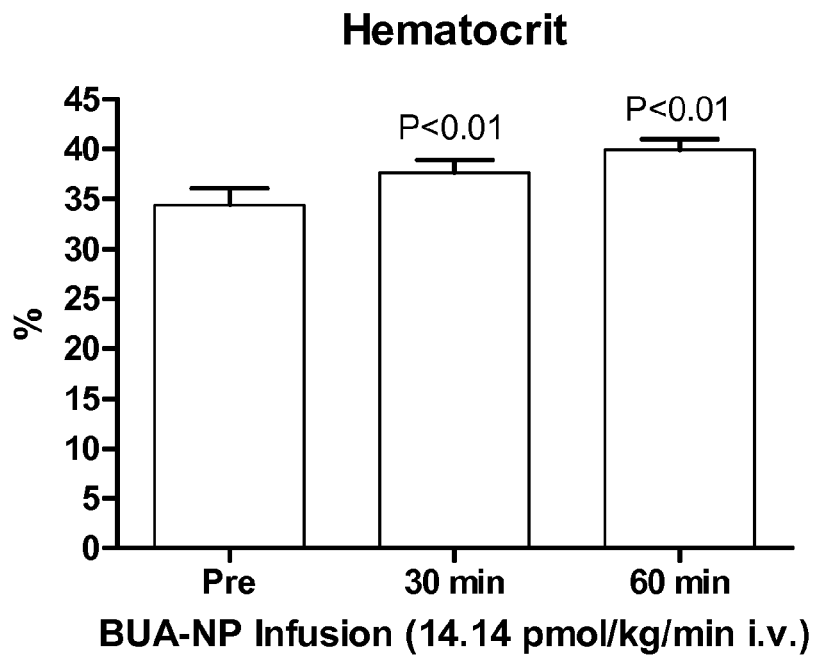
FIG. 49 is a graph plotting hematocrit levels before and during BUA-NP infusion (n=6).
Figure 50:
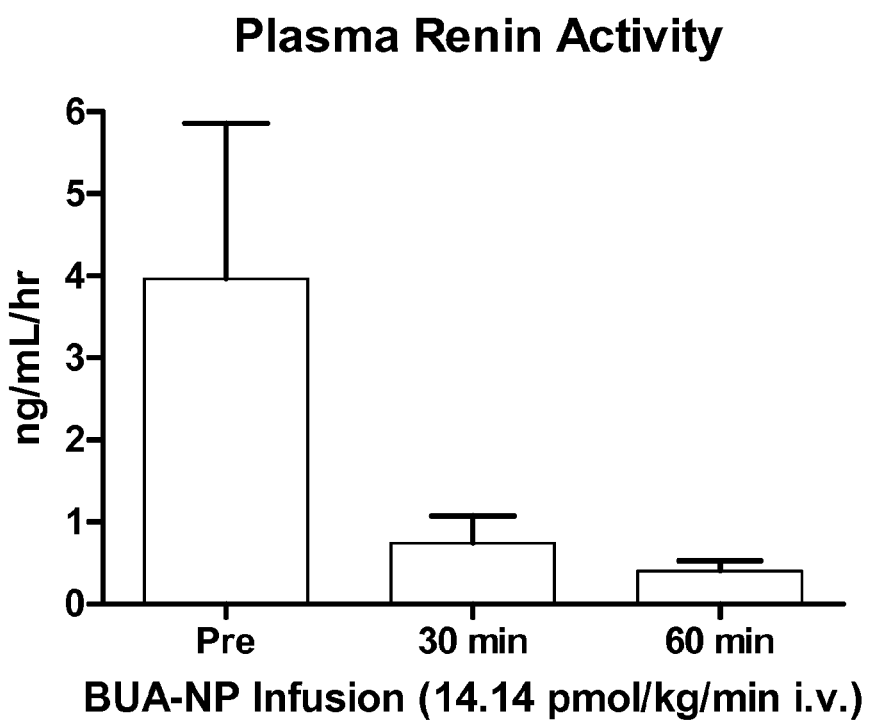
FIG. 50 is a graph plotting plasma renin activity before and during BUA-NP infusion (n=5).
Figure 51:
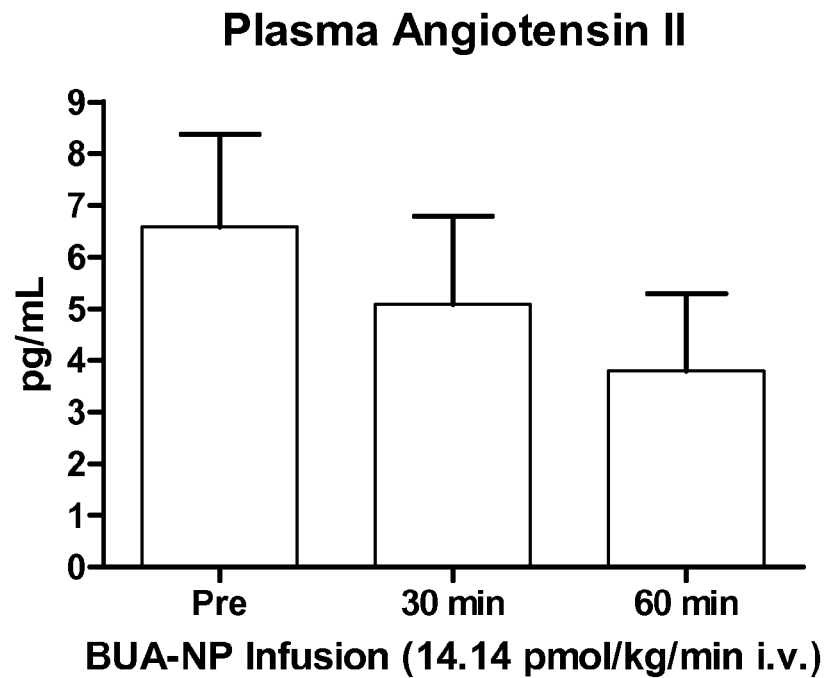
FIG. 51 is a graph plotting plasma angiotensin II before and during BUA-NP infusion (n=5).
Figure 52:
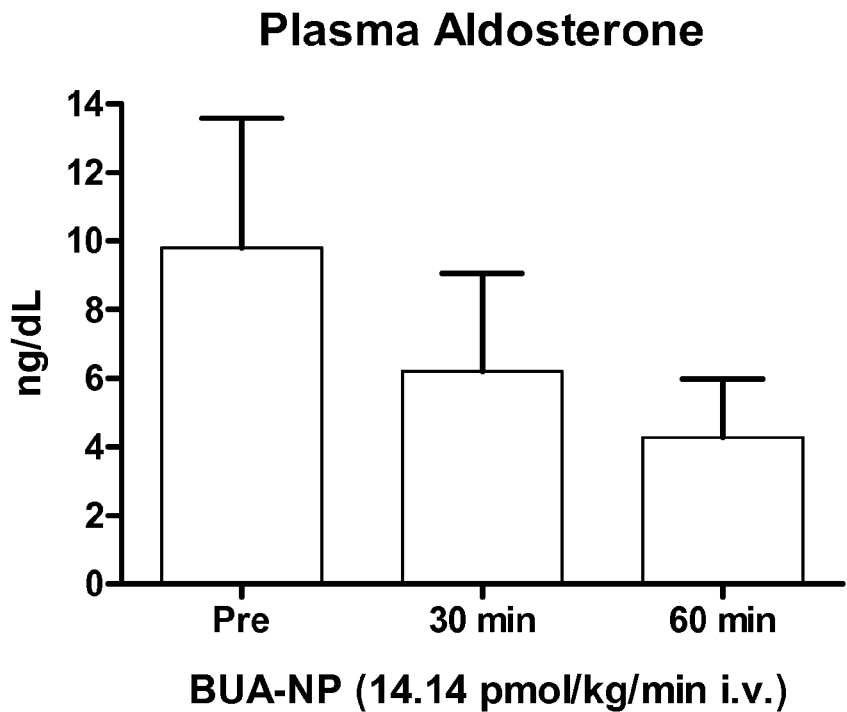
FIG. 52 is a graph plotting plasma aldosterone before and during BUA-NP infusion (n=3).
Figure 53:
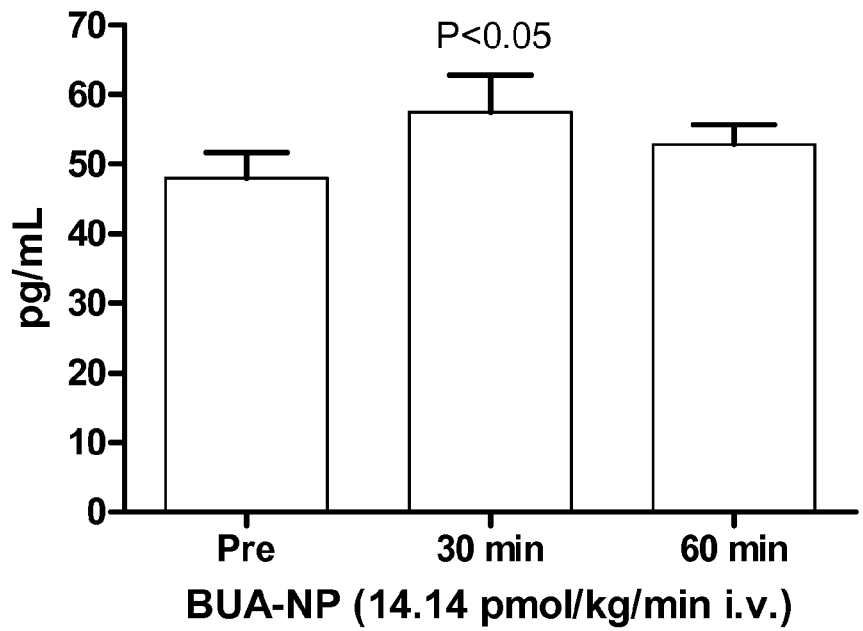
FIG. 53 is a graph plotting plasma ANP immunoreactivity before and during BUA-NP infusion (n=6).
Figure 54:
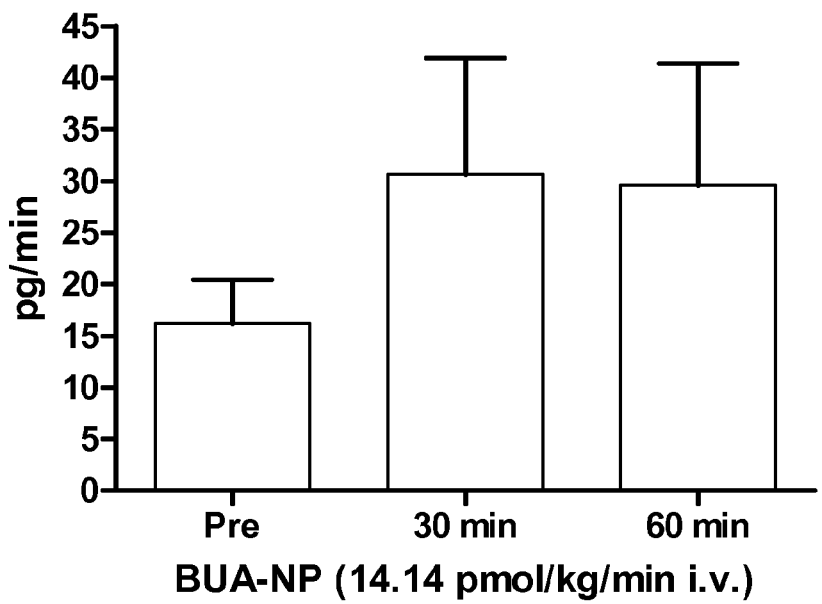
FIG. 54 is a graph plotting urinary excretion of ANP before and during BUA-NP infusion (n=6).
Figure 55:
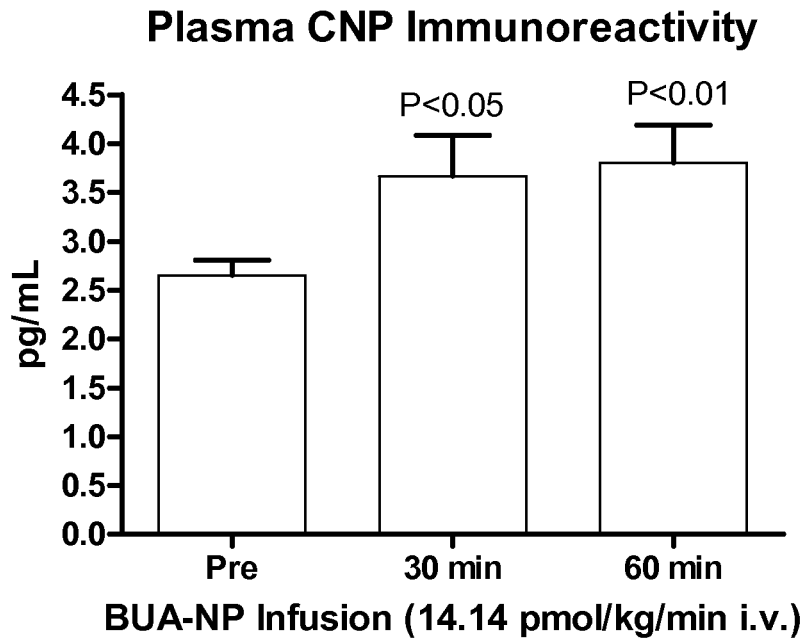
FIG. 55 is a graph plotting plasma CNP immunoreactivity before and during BUA-NP infusion (n=6).
Figure 56:
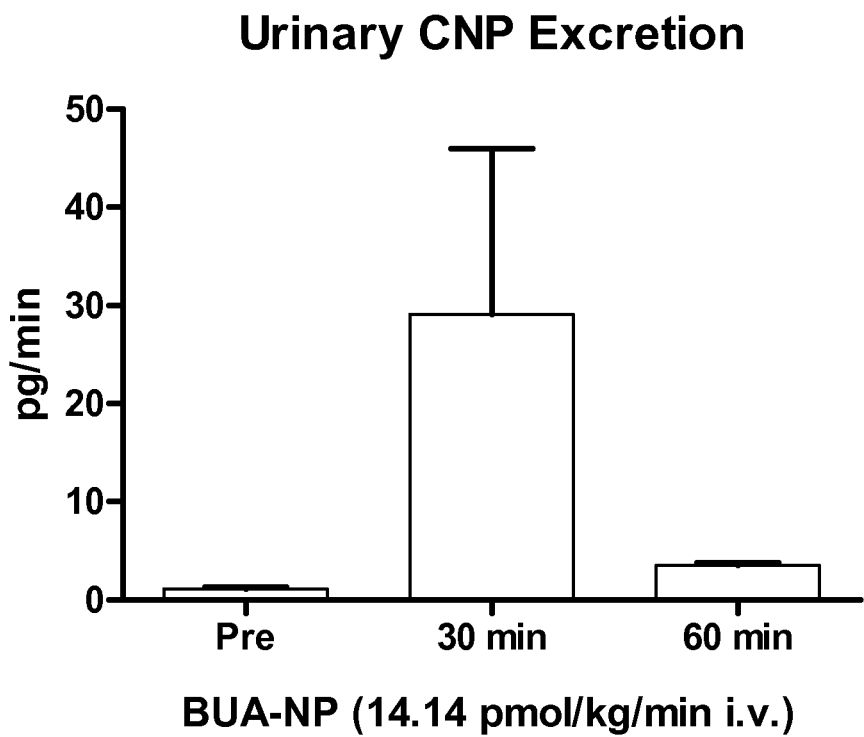
FIG. 56 is a graph plotting urinary CNP excretion before and during BUA-NP infusion (n=6).

This document relates to natriuretic polypeptides. For example, this document provides methods and materials related to natriuretic polypeptides and the use of natriuretic polypeptides to treat cardiovascular conditions (e.g., acute decompensated heart failure, acute coronary syndromes, and ventricular remodeling post-myocardial infarction) and renal conditions (e.g., perioperative renal dysfunction, renal dysfunction secondary to heart failure, and diabetic nephropathy).

A polypeptide provided herein can have any sequence and can have any length. For example, a polypeptide provided herein can include the sequence set forth in SEQ ID NO:1, SEQ ID NO:2, and SEQ ID NO:3. In some cases, a polypeptide provided herein can contain an amino acid sequence that aligns to (a) the sequence set forth in SEQ ID NO:1 with three or less (e.g., two or less, one, or zero) amino acid additions, deletions, substitutions, or combinations thereof, (b) the sequence set forth in SEQ ID NO:2 with five or less (e.g., four or less, three or less, two or less, one, or zero) amino acid additions, deletions, substitutions, or combinations thereof and (c) the sequence set forth in SEQ ID NO:3 with three or less (e.g., two or less, one, or zero) amino acid additions, deletions, substitutions, or combinations thereof. For example, a polypeptide provided herein can contain the sequence set forth in SEQ ID NO:1 with the exception that the first serine residue or the last serine residue of SEQ ID NO:1 is deleted or replaced with a different amino acid residue.

In some cases, a polypeptide provided herein can include the sequence set forth in SEQ ID NO:6, SEQ ID NO:2, and SEQ ID NO:7. In some cases, a polypeptide provided herein can contain an amino acid sequence that aligns to (a) the sequence set forth in SEQ ID NO:6 with three or less (e.g., two or less, one, or zero) amino acid additions, deletions, substitutions, or combinations thereof, (b) the sequence set forth in SEQ ID NO:2 with five or less (e.g., four or less, three or less, two or less, one, or zero) amino acid additions, deletions, substitutions, or combinations thereof and (c) the sequence set forth in SEQ ID NO:7 with three or less (e.g., two or less, one, or zero) amino acid additions, deletions, substitutions, or combinations thereof. For example, a polypeptide provided herein can contain the sequence set forth in SEQ ID NO:6 with the exception that the first occurring proline residue or the last occurring serine residue of SEQ ID NO:6 is deleted or replaced with a different amino acid residue. In some cases, a polypeptide provided herein can contain an amino acid sequence that aligns to (a) the sequence set forth in SEQ ID NO:6 with three or less (e.g., two or less, one, or zero) amino acid additions, deletions, substitutions, or combinations thereof, provided that the polypeptide contains the TAPR amino acid sequence, (b) the sequence set forth in SEQ ID NO:2 with five or less (e.g., four or less, three or less, two or less, one, or zero) amino acid additions, deletions, substitutions, or combinations thereof and (c) the sequence set forth in SEQ ID NO:7 with three or less (e.g., two or less, one, or zero) amino acid additions, deletions, substitutions, or combinations thereof. The presence of an N-terminal TAPR amino acid sequence can enhance the cGMP-activating and renal actions of the polypeptide.

Amino acid substitutions can be conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. After making an amino acid substitution, the activities of the polypeptide containing the amino acid substitution can be assessed using the assays described herein.

In some cases, a polypeptide provided herein can contain (a) a first amino acid sequence that either is set forth in SEQ ID NO:1 or aligns to the sequence set forth in SEQ ID NO:1 with three or less (e.g., two or less, one, or zero) amino acid deletions, substitutions, or combinations thereof, (b) a second amino acid sequence that either is set forth in SEQ ID NO:2 or aligns to the sequence set forth in SEQ ID NO:2 with five or less (e.g., four or less, three or less, two or less, one, or zero) amino acid additions, substitutions, or combinations thereof, and (c) a third amino acid sequence that either is set forth in SEQ ID NO:3 or aligns to the sequence set forth in SEQ ID NO:3 with three or less (e.g., two or less, one, or zero) amino acid deletions, substitutions, or combinations thereof. For example, a polypeptide provided herein can comprise or consist of the sequence set forth in SEQ ID NO:4.

In some cases, a polypeptide provided herein can contain (a) a first amino acid sequence that either is set forth in SEQ ID NO:6 or aligns to the sequence set forth in SEQ ID NO:6 with three or less (e.g., two or less, one, or zero) amino acid deletions, substitutions, or combinations thereof, (b) a second amino acid sequence that either is set forth in SEQ ID NO:2 or aligns to the sequence set forth in SEQ ID NO:2 with five or less (e.g., four or less, three or less, two or less, one, or zero) amino acid additions, substitutions, or combinations thereof, and (c) a third amino acid sequence that either is set forth in SEQ ID NO:7 or aligns to the sequence set forth in SEQ ID NO:7 with three or less (e.g., two or less, one, or zero) amino acid deletions, substitutions, or combinations thereof. For example, a polypeptide provided herein can comprise or consist of the sequence set forth in SEQ ID NO:5.

A polypeptide provided herein can have any length. For example, a polypeptide provided herein can be between 23 and 45 (e.g., between 25 and 45, between 26 and 44, between 27 and 43, between 28 and 42, between 29 and 41, between 30 and 40, between 31 and 39, between 23 and 35, between 25 and 30, or between 30 and 35) amino acid residues in length. It will be appreciated that a polypeptide with a length of 25 or 45 amino acid residues is a polypeptide with a length between 25 and 45 amino acid residues.

In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

A polypeptide provide herein can be obtained by expression of a recombinant nucleic acid encoding the polypeptide or by chemical synthesis (e.g., using solid phase polypeptide synthesis methods or an peptide synthesizer such as an ABI 431A Peptide Synthesizer; Applied Biosystems; Foster City, Calif.). For example, standard recombinant technology using expression vectors encoding a polypeptide provide herein can be used. The resulting polypeptides then can be purified using, for example, affinity chromatographic techniques and HPLC. The extent of purification can be measured by any appropriate method, including but not limited to: column chromatography, polyacrylamide gel electrophoresis, or high-performance liquid chromatography. A polypeptide provide herein can be designed or engineered to contain a tag sequence that allows the polypeptide to be purified (e.g., captured onto an affinity matrix). For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that can be used include enzymes that aid in the detection of the polypeptide, such as alkaline phosphatase.

A polypeptide provided herein can be produced to contain three regions, a first region that includes an N-terminus (e.g., an N-terminus sequence from a human ANP or urodilatin polypeptide), a second region that includes a ring structure of a mature natriuretic polypeptide such as a human BNP polypeptide, and third region that includes a C-terminus (e.g., the C-terminus sequence from a human ANP or urodilatin polypeptide). For example, a polypeptide provided herein can be produced to contain a first region that includes an N-terminus sequence from a human ANP or urodilatin polypeptide, a second region that includes a ring structure of a mature natriuretic polypeptide such as a human BNP polypeptide, and third region that includes the C-terminus sequence from a human ANP or urodilatin polypeptide.

A polypeptide provided herein can be used to treat cardiovascular diseases, congestive heart failure, myocardial infarction, coronary artery diseases, renal diseases, hepatic diseases, cancer, metabolic diseases, or combinations thereof. For example, a BAA-NP polypeptide having the amino acid sequence set forth in SEQ ID NO:4 or a BUA-NP polypeptide having the amino acid sequence set forth in SEQ ID NO:5 can be administered to a human having coronary artery disease under conditions wherein the severity of the human's coronary artery disease symptoms is reduced.

A polypeptide provided herein can be formulated as a pharmaceutical composition by admixture with pharmaceutically acceptable non-toxic excipients or carriers. Such compositions can be administered to a subject in need thereof in an amount effective to treat, for example, heart, liver, kidney, or other sodium retaining conditions. Pharmaceutical compositions can be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration can be prepared as desired using appropriate methods.

Formulations for parenteral administration can include as common excipients, sterile water, saline, polyalkylene glycols such as polyethylene glycol, oils of vegetable origin, hydrogenated naphthalenes, and combinations thereof. In some cases, biocompatible, biodegradable lactide polymer, lactide/glycolide copolymer, polyoxethylene-polyoxypropylene copolymers, or combinations thereof can be used as excipients for controlling the release of the polypeptide in vivo. Other suitable parenteral delivery systems that can be used include, without limitation, ethylene-vinyl acetate copolymer particles, osmotic pumps, implantable infusion systems, liposomes, and combinations thereof. Formulations for inhalation administration can include excipients such as lactose. Inhalation formulations can be aqueous solutions containing, for example, polyoxyethylene-9-lauryl ether, glycocholate, deoxycholate, or combinations thereof, or they can be oily solutions for administration in the form of nasal drops. If desired, a composition containing a polypeptide provided herein can be formulated as gel to be applied intranasally. Formulations for parenteral administration can include glycocholate for buccal administration.

For oral administration, tablets or capsules can be prepared using appropriate methods with pharmaceutically acceptable excipients such as binding agents (e.g., pregelatinized maize starch, polyvinylpyrrolidone, or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated using appropriate methods. Preparations for oral administration can be formulated to give controlled release of the polypeptide.

Nasal preparations can be presented in a liquid form or as a dry product. Nebulised aqueous suspensions or solutions can include carriers or excipients to adjust pH and/or tonicity.

Nucleic Acids Encoding Polypeptides

This document also provides isolated nucleic acids that encode one or more of the polypeptides provided herein. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid (e.g., a nucleic acid encoding a polypeptide comprising or consisting of the amino acid sequence set forth in SEQ ID NO:4 or SEQ ID NO:5) can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence. A nucleic acid existing among hundreds to millions of other nucleic acids within, for example, cDNA libraries or genomic libraries, or gel slices containing a genomic DNA restriction digest, is not to be considered an isolated nucleic acid.

As used herein, the term "nucleic acid" refers to both RNA and DNA, including mRNA, cDNA, genomic DNA, synthetic (e.g., chemically synthesized) DNA, and nucleic acid analogs. The nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller *Antisense Nucleic Acid Drug Dev.*, 7:187-195 (1997); and Hyrup et al. *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

A nucleic acid provided herein can comprise or consist of a sequence that encodes the amino acid sequence set forth in SEQ ID NO:4 or SEQ ID NO:5. For example, such a nucleic acid can contain the human nucleic acid sequence for BNP and ANP engineered to encode the amino acid sequence set forth in SEQ ID NO:4. In some cases, such a nucleic acid can contain the human nucleic acid sequence for BNP, urodilatin, and ANP engineered to encode the amino acid sequence set forth in SEQ ID NO:5.

Typically, an isolated nucleic acid provided herein is at least 10 nucleotides in length (e.g., 10, 15, 20, 25, 30, 35, 40, 50, 75, 100, 200, 300, 350, 400, or more nucleotides in length). Nucleic acid molecules that are less than full-length can be useful, for example, as primers or probes for diagnostic purposes. Isolated nucleic acid molecules can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 15 to 50 nucleotides in length, but can range from 10 nucleotides to hundreds of nucleotides in length. For example, a primer can be 12, 15, 16, 17, 18, 19, 20, 21, 22, 23, 24, 25, 26, 27, 28, 29, 30, 35, 40, or 45 nucleotides in length. A primer can be purified from a restriction digest by conventional methods, or can be chemically synthesized. Primers typically are single-stranded for maximum efficiency in amplification, but a primer can be double-stranded. Double-stranded primers are first denatured (e.g., treated with heat) to separate the strands before use in amplification. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids as described elsewhere (Lewis, *Genetic Engineering News*, 12(9):1 (1992); Guatelli et al., *Proc. Natl. Acad. Sci. USA*, 87:1874-1878 (1990); and Weiss, *Science*, 254:1292 (1991)).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, a nucleic acid sequence encoding a polypeptide having the sequence set forth in SEQ ID NO:1, 2, 3, 4, 5, 6, or 7 can be mutated using standard techniques such as, for example, oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992. Such mutations include additions, deletions, substitutions, and combinations thereof.

Vectors and Host Cells

This document also provides vectors containing a nucleic acid provided herein. As used herein, a "vector" is a replicon, such as a plasmid, phage, or cosmid, into which another DNA segment can be inserted so as to bring about the replication of the inserted segment. A vector can be an expression vector. An "expression vector" is a vector that includes one or more expression control sequences, and an "expression control sequence" is a DNA sequence that controls and regulates the transcription and/or translation of another DNA sequence.

In an expression vector provided herein, the nucleic acid can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it can be necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, Wis.), Clontech Laboratories (Mountain View, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid molecule and/or nucleic acid vector provided herein. The term "host cell" refers to prokaryotic cells and eukaryotic cells into which a nucleic acid molecule or vector can be introduced. Any method can be used to introduce nucleic acid into a cell. For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document provides methods and materials for detecting a polypeptide provided herein. Such methods and materials can be used to monitor polypeptide levels within a mammal receiving the polypeptide as a therapeutic. A polypeptide provided herein (e.g., a BAA-NP polypeptide having the amino acid sequence set forth in SEQ ID NO:4 or a BUA-NP polypeptide having the amino acid sequence set forth in SEQ ID NO:5) can be detected, for example, immunologically using one or more antibodies. As used herein, the term "antibody" includes intact molecules as well as fragments thereof that are capable of binding to an epitopic determinant of a polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and F(ab)$_2$ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for a polypeptide provided herein (e.g., a BAA-NP polypeptide having the amino acid sequence set forth in SEQ ID NO:4 or a BUA-NP polypeptide having the amino acid sequence set forth in SEQ ID NO:5) can be generated by known techniques. For example, F(ab')2 fragments can be produced by pepsin digestion of the antibody molecule; Fab fragments can be generated by reducing the disulfide bridges of F(ab')2 fragments. In some cases, Fab expression libraries can be constructed. See, for example, Huse et al., *Science*, 246:1275 (1989). Once produced, antibodies or fragments thereof can be tested for recognition of a polypeptide provided herein by standard immunoassay methods including ELISA techniques, radioimmunoassays, and Western blotting. See, *Short Protocols in Molecular Biology*, Chapter 11, Green Publishing Associates and John Wiley & Sons, Edited by Ausubel, F. M et al., 1992.

In immunological assays, an antibody having specific binding affinity for a polypeptide provided herein or a secondary antibody that binds to such an antibody can be labeled, either directly or indirectly. Suitable labels include, without limitation, radionuclides (e.g., $^{125}$I, $^{131}$I, $^{35}$S, $^{3}$H, $^{32}$P, $^{33}$P, or $^{14}$C), fluorescent moieties (e.g., fluorescein, FITC, PerCP, rhodamine, or PE), luminescent moieties (e.g., Qdot™ nanoparticles supplied by Invitrogen (Carlsbad, Calif.)), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting a polypeptide provided herein generally include contacting a biological sample with an antibody that binds to a polypeptide provided herein and detecting binding of the polypeptide to the antibody. For example, an antibody having specific binding affinity for a polypeptide provided herein can be immobilized on a solid substrate by any of a variety of methods known in the art and then exposed to the biological sample. Binding of the polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). In some cases, the antibody can be labeled and detected as described above. A standard curve using known quantities of a polypeptide provided herein can be generated to aid in the quantitation of the levels of the polypeptide.

In some embodiments, a "sandwich" assay in which a capture antibody is immobilized on a solid substrate can be used to detect the presence, absence, or level of a polypeptide provided herein. The solid substrate can be contacted with the biological sample such that any polypeptide of interest in the sample can bind to the immobilized antibody. The presence, absence, or level of the polypeptide bound to the antibody can be determined using a "detection" antibody having specific binding affinity for the polypeptide. In some embodiments, a capture antibody can be used that has binding affinity for ANP, BNP, or urodilatin as well as a polypeptide provided herein. In this embodiment, a detection antibody can be used that has specific binding affinity for a particular polypeptide provided herein (e.g., a BAA-NP polypeptide having the amino acid sequence set forth in SEQ ID NO:4 or a BUA-NP polypeptide having the amino acid sequence set forth in SEQ ID NO:5). It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a polypeptide provided herein can be produced through standard methods. For example, a polypeptide can be recombinantly produced as described above, can be purified from a biological sample (e.g., a heterologous expression system), or can be chemically synthesized, and used to immunize host animals, including rabbits, chickens, mice, guinea pigs, or rats. For example, a polypeptide having the amino acid sequence set forth in SEQ ID NO:4 or SEQ ID NO:5, or fragments thereof that are at least six amino acids in length, can be used to immunize an animal Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., *Nature,* 256:495 (1975), the human B-cell hybridoma technique (Kosbor et al., *Immunology Today,* 4:72 (1983); Cole et al., *Proc. Natl. Acad. Sci. USA,* 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

Other techniques for detecting a polypeptide provided herein include mass-spectrophotometric techniques such as electrospray ionization (ESI), and matrix-assisted laser desorption-ionization (MALDI). See, for example, Gevaert et al., *Electrophoresis,* 22(9):1645-51 (2001); Chaurand et al., *J. Am. Soc. Mass Spectrom.,* 10(2):91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

The invention will be further described in the following examples, which do not limit the scope of the invention described in the claims.

EXAMPLES

A polypeptide with the sequence set forth in FIG. 1 was designed and synthesized using an ABI 431A Peptide Synthesizer. This polypeptide is referred to as a BAA-NP polypeptide (FIG. 1). The synthesized BAA-NP polypeptide was confirmed by high-performance liquid chromatography and mass spectrometry. Its molecular weight was 3158.60, and its amino acid sequence is SLRRSSCFGRKM-DRISSSSG-LGCNSFRY (SEQ ID NO:4) with a disulfide bridge joining the Cys residues.

A polypeptide with the sequence set forth in FIG. 2 was designed and synthesized using an ABI 431A Peptide Synthesizer. This polypeptide is referred to as a BUA-NP polypeptide (FIG. 2). The synthesized BUA-NP polypeptide was confirmed by high-performance liquid chromatography and mass spectrometry. Its molecular weight was 3582.08, and its amino acid sequence is TAPRSLRRSSCFGRKM-DRIS-SSSGLGCNSFRY (SEQ ID NO:5) with a disulfide bridge joining the Cys residues.

BAA-NP and BUA-NP were reconstituted in normal saline and were infused at 1 mL/minute. Dogs were maintained on a $Na^+$-controlled diet (Hill's i/d® canine diet, Hill's Pet Nutrition, Inc., Topeka, Kans.). In the evening before the experiment, the dog was fasted with ad lib access to water and was given lithium carbonate 300 mg orally for assessment of renal tubular function on the next day.

On the day of the experiment, the dog was anesthetized with pentobarbital sodium (induction 6-20 mg/kg i.v., maintenance 5-15 mg/kg/h i.v.) and fentanyl (0.04-0.12 mg/kg i.v., maintenance 0.04-0.18 mg/kg/h), and was intubated and mechanically ventilated (Harvard Apparatus, Holliston, Mass.) with 3 L/minute of $O_2$ (tidal volume 15 mL/kg, 12 cycles/minute). The femoral artery was cannulated for blood pressure monitoring and for blood sampling. The femoral vein was cannulated for infusion of inulin and normal saline. The saphenous vein was cannulated for polypeptide infusion. A balloon-tipped thermodilution catheter (Edwards Lifesciences, Irvine, Calif.) was used for monitoring hemodynamics and body temperature (maintained at 38±1° C.). Cardiac output (CO) was measured in triplicate and averaged (model 9510-A, American Edwards Laboratories, Irvine, Calif.). Hemodynamic data were digitally recorded and analyzed (Sonometrics Corporation, London, ON). The left kidney was exposed via a flank incision. The ureter was cannulated for timed urine collection. An electromagnetic flow probe was placed on the renal artery for measuring renal blood flow (Burnett et al., *Am. J. Physiol.,* 247(5 Pt 2):F863-6 (1984)). A weight-adjusted bolus of inulin was given, followed by an inulin infusion (1 mL/minute) to achieve plasma levels of 40-60 mg/dL (Burnett et al., *Am. J. Physiol.,* 247(5 Pt 2):F863-6 (1984); Chen et al., *Am. J. Physiol. Regul. Integr. Comp. Physiol.,* 288(5):R1093-7 (2005); and Margulies et al., *J. Clin. Invest.,* 88(5):1636-42 (1991)), for measuring GFR by inulin clearance. Normal saline was infused (1 mL/minute) and was temporarily discontinued during peptide infusion (1 mL/minute).

Following equilibration of approximately 60 minutes in duration, the BAA-NP or BUA-NP polypeptide was infused for 75 minutes. Hemodynamic and renal data, as well as blood and urine samples, were collected for each 30-minute clearance: pre-infusion, at 30 and 60 minutes of infusion (time denotes mid-clearance). Insulin clearance was used for measuring glomerular filtration rate (GFR). The lithium clearance technique was used for quantifying proximal and distal fractional reabsorption of $Na^+$ (PFRNa and DFRNa, respectively).

Plasma and urinary ANP, CNP, and cGMP were measured by radioimmunoassays (RIA) (Chen et al., *Am. J. Physiol. Regul. Integr. Comp. Physiol.,* 288(5):R1093-7 (2005); Burnett et al., *Science,* 231(4742):1145-7 (1986); Steiner et al., *J. Biol. Chem.,* 247(4):1106-13 (1972); Supaporn et al., *Kidney Int.,* 50(5):1718-25 (1996); and Cataliotti et al., *Am. J. Physiol.,* 283(3):F464-72 (2002)). Plasma renin activity (Haber et al., *J. Clin. Endocrinol. Metab.,* 29(10):1349-55 (1969)), angiotensin II (Luchner et al., *Hypertension,* 28(3): 472-7 (1996)), and aldosterone (Sancho and Haber, *J. Clin. Endocrinol. Metab.,* 47(2):391-6 (1978)) were quantified. Plasma and urinary lithium levels were measured by flame emission spectrophotometry (model 357, Instrumentation Laboratory, Wilmington, Mass.) (Margulies et al., *J. Clin. Invest.,* 88(5):1636-42 (1991)). The lithium clearance technique (CLLi) was used to assess PFRNa and DFRNa as follows (Chen et al., *Am. J. Physiol. Regal. Integr. Comp. Physiol.,* 288(5):R1093-7 (2005)): PFRNa=[1-(CLLi/GFR)]×100 and DFRNa=[(CLLi−CLNa)/CLLi]×100, where CLLi=[urine $Li^+$]×urine flow/[plasma $Li^+$] and CLNa=[urine $Na^+$]×urine flow/[plasma $Na^+$]. Net renal production of cGMP was determined (Margulies et al., *J. Clin. Invest.,* 88(5):1636-42 (1991)): (urinary cGMP×urine flow rate)−(plasma cGMP×GFR).

In addition, comparisons were made with an equimolar dose of human BNP (n=7) for mean arterial pressure and renal perfusion pressure (the latter was calculated by mean arterial pressure−right atrial pressure).

Comparisons of the data at 30 and 60 minutes of infusion vs. pre-infusion were made by one-way repeated measures ANOVA followed by Dunnett's multiple comparison test. Between-group comparisons were made by two-way ANOVA. Additional analyses were made by comparing changes in renal perfusion pressure and changes in mean arterial pressure from the respective pre-infusion values (i.e., baselines) among BAA-NP, BUA-NP, and BNP using one-way ANOVA.

Figure 57:
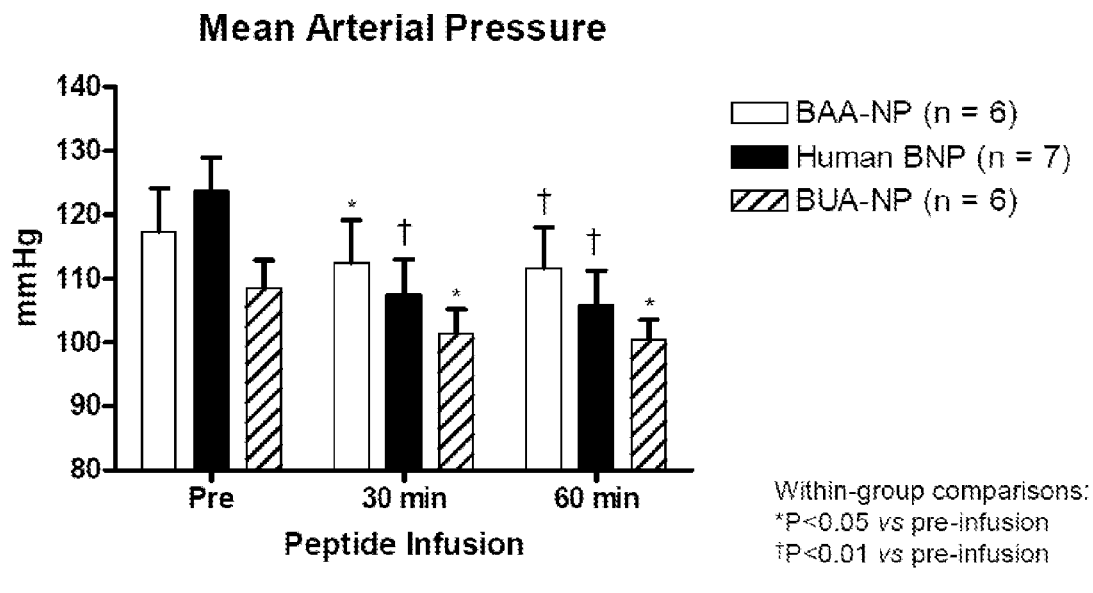
FIG. 57 is a graph plotting mean arterial pressure for the indicated polypeptides. The comparison was performed using an equimolar dose of human BNP.
Figure 58:
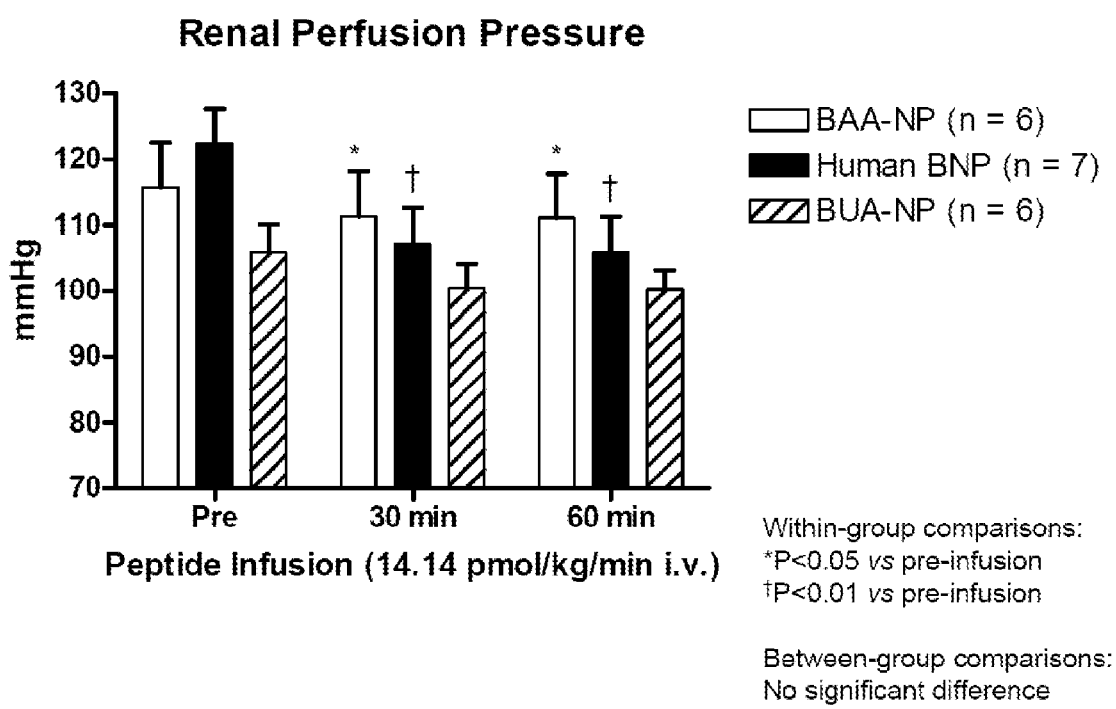
FIG. 58 is a graph plotting renal perfusion pressure for the indicated polypeptides. The comparison was performed using an equimolar dose of human BNP.
Figure 59:
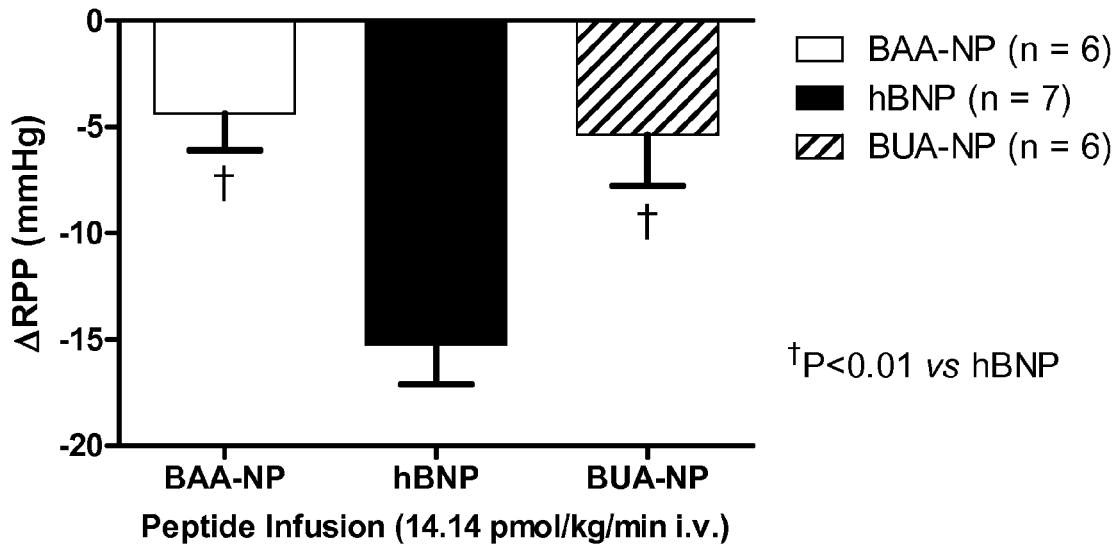
FIG. 59 is a graph plotting the change in renal perfusion pressure from baseline at 30 minutes of infusion with the indicated peptide.
Figure 60:
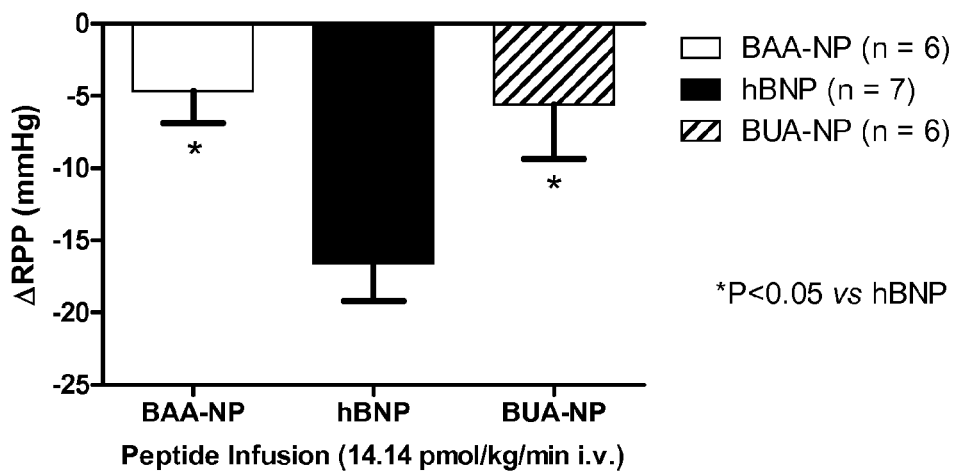
FIG. 60 is a graph plotting the change in renal perfusion pressure from baseline at 30 minutes of infusion with the indicated peptide.
Figure 61:
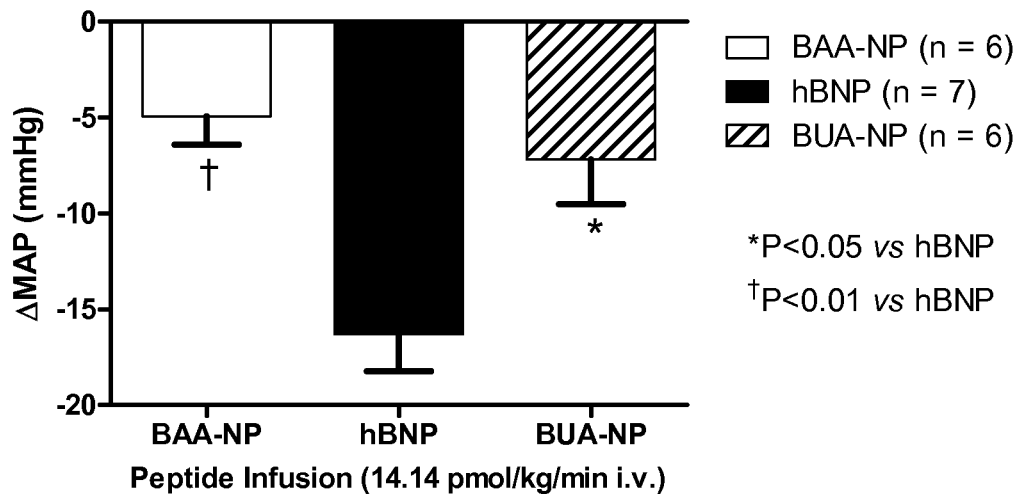
FIG. 61 is a graph plotting the change in mean arterial pressure from baseline at 30 minutes of infusion with the indicated peptide.
Figure 62:
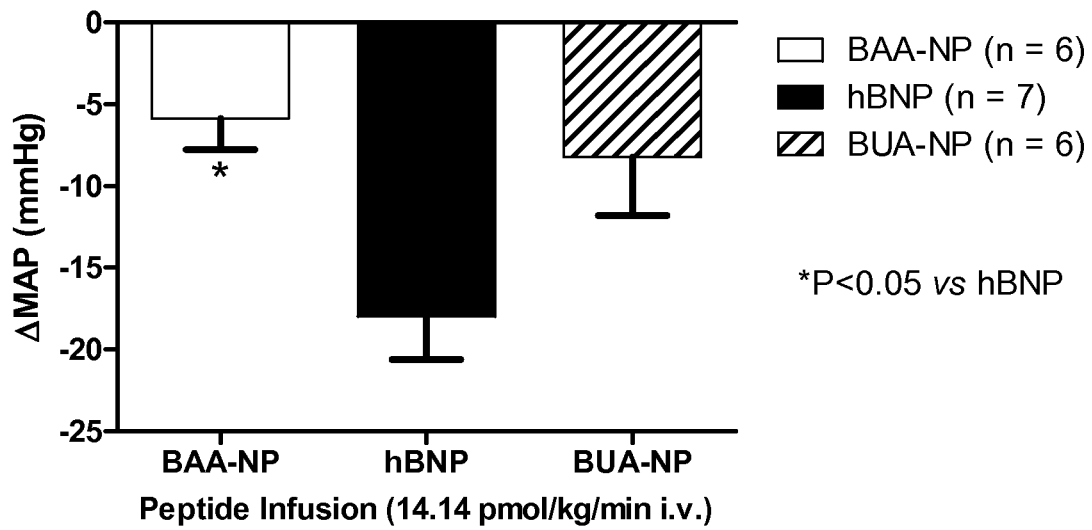
FIG. 62 is a graph plotting the change in mean arterial pressure from baseline at 60 minutes of infusion with the indicated peptide.
Figure 63:
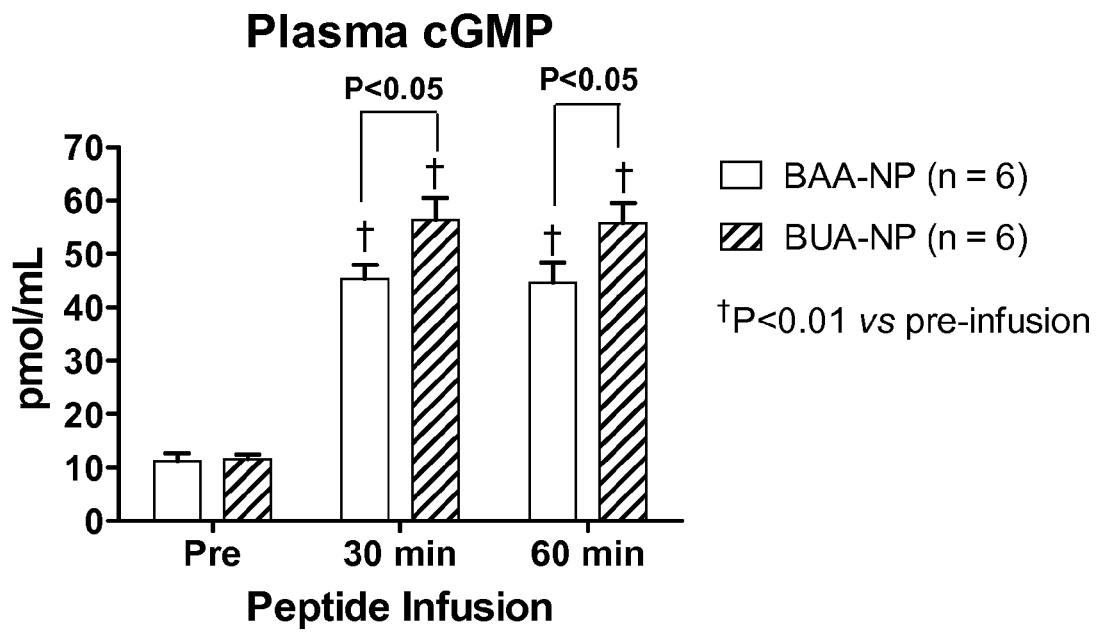
FIG. 63 is a graph plotting plasma cGMP levels (pmol/mL) before and after (30 minutes and 60 minutes) infusion with the indicated peptides.
Figure 64:
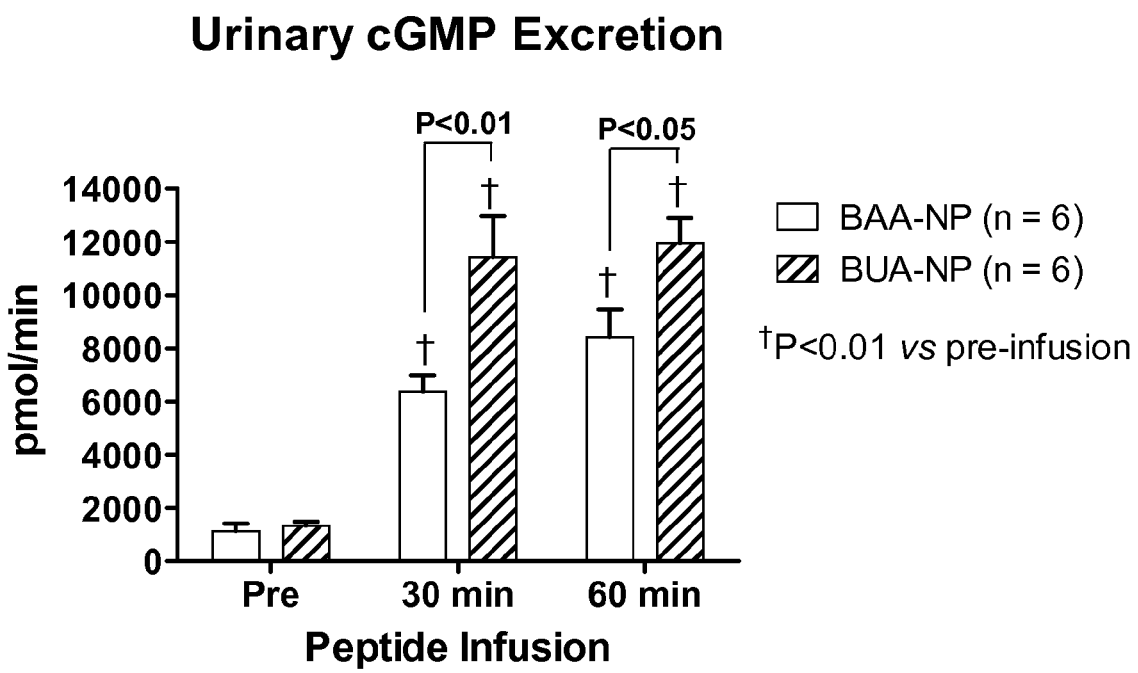
FIG. 64 is a graph plotting urinary cGMP excretion (pmol/min) before and after (30 minutes and 60 minutes) infusion with the indicated peptides.
Figure 65:
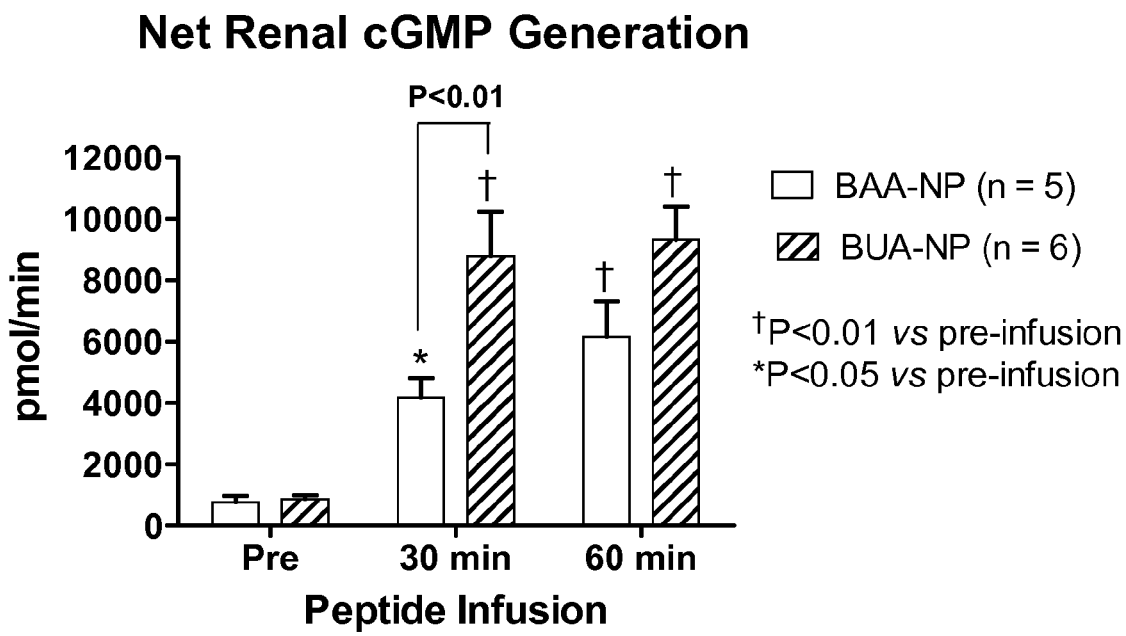
FIG. 65 is a graph plotting net renal cGMP generation (pmol/min) before and after (30 minutes and 60 minutes) infusion with the indicated peptides.
Figure 66:
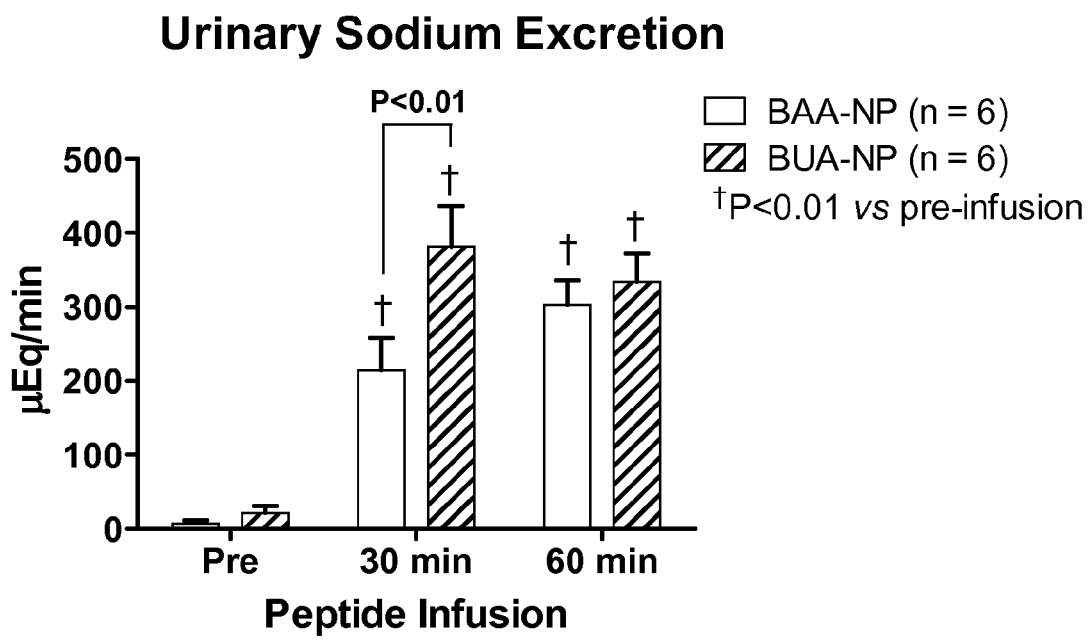
FIG. 66 is a graph plotting urinary sodium excretion (µEq/min) before and after (30 minutes and 60 minutes) infusion with the indicated peptides.
Figure 67:
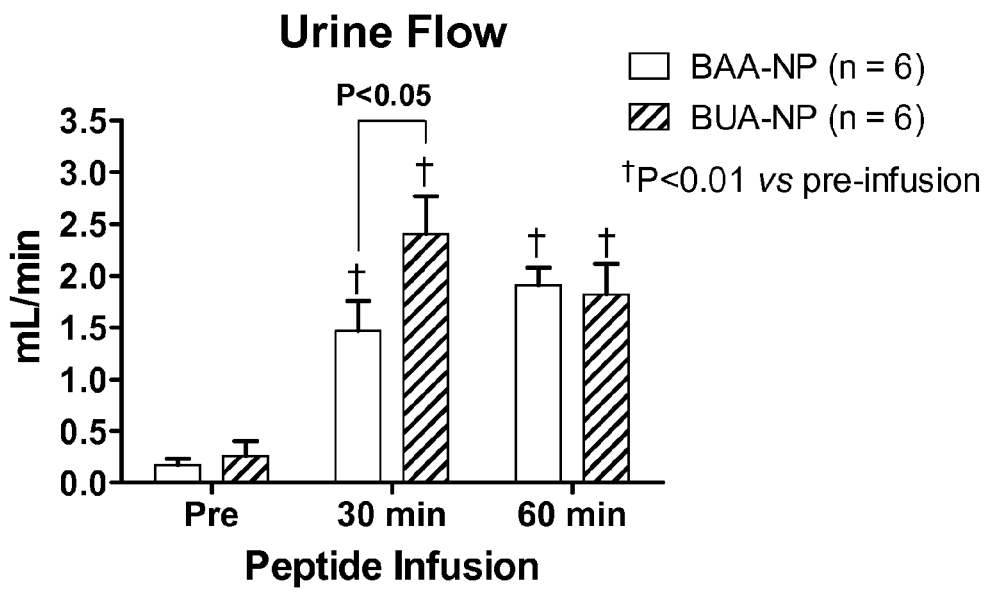
FIG. 67 is a graph plotting urine flow (mL/min) before and after (30 minutes and 60 minutes) infusion with the indicated peptides.
Figure 68:
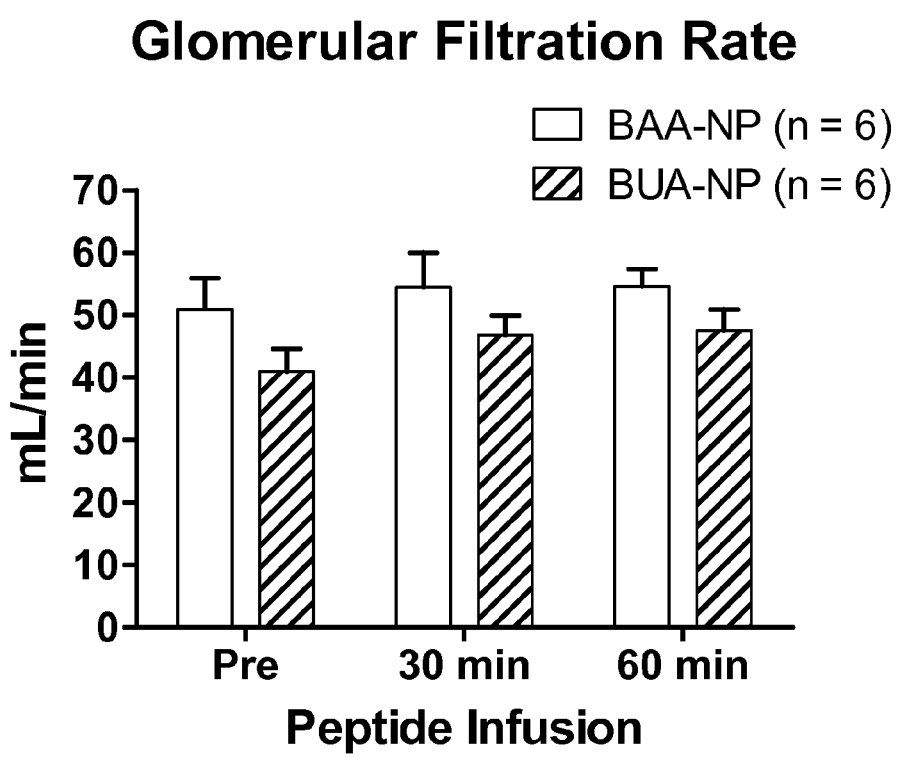
FIG. 68 is a graph plotting glomerular filtration rate (mL/min) before and after (30 minutes and 60 minutes) infusion with the indicated peptides.
Figure 69:
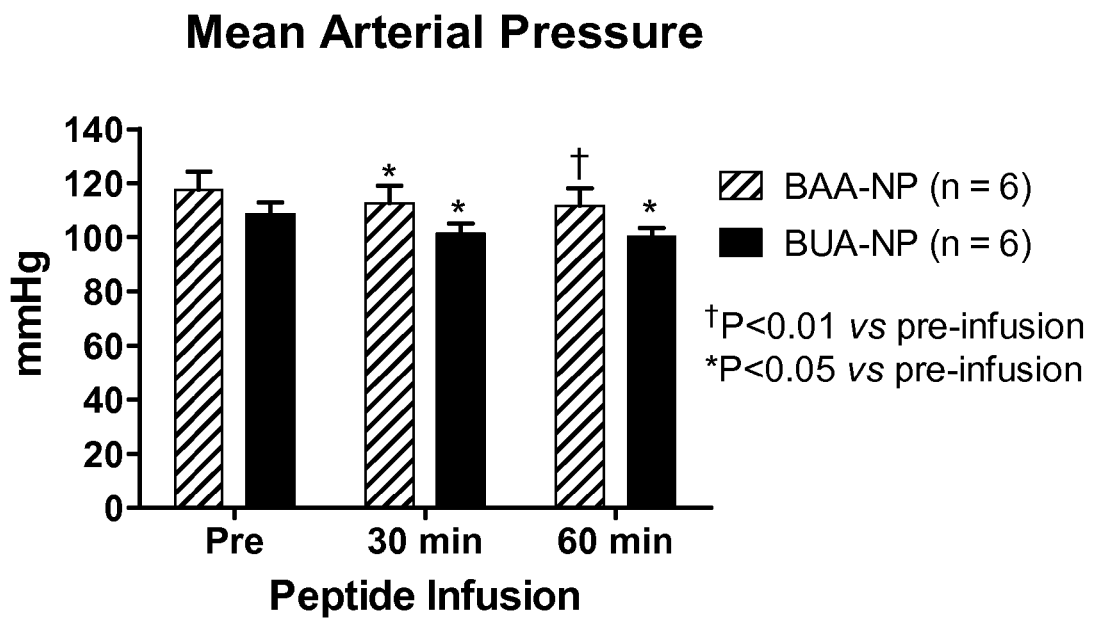
FIG. 69 is a graph plotting mean arterial pressure (mmHg) before and after (30 minutes and 60 minutes) infusion with the indicated peptides.
Figure 70:
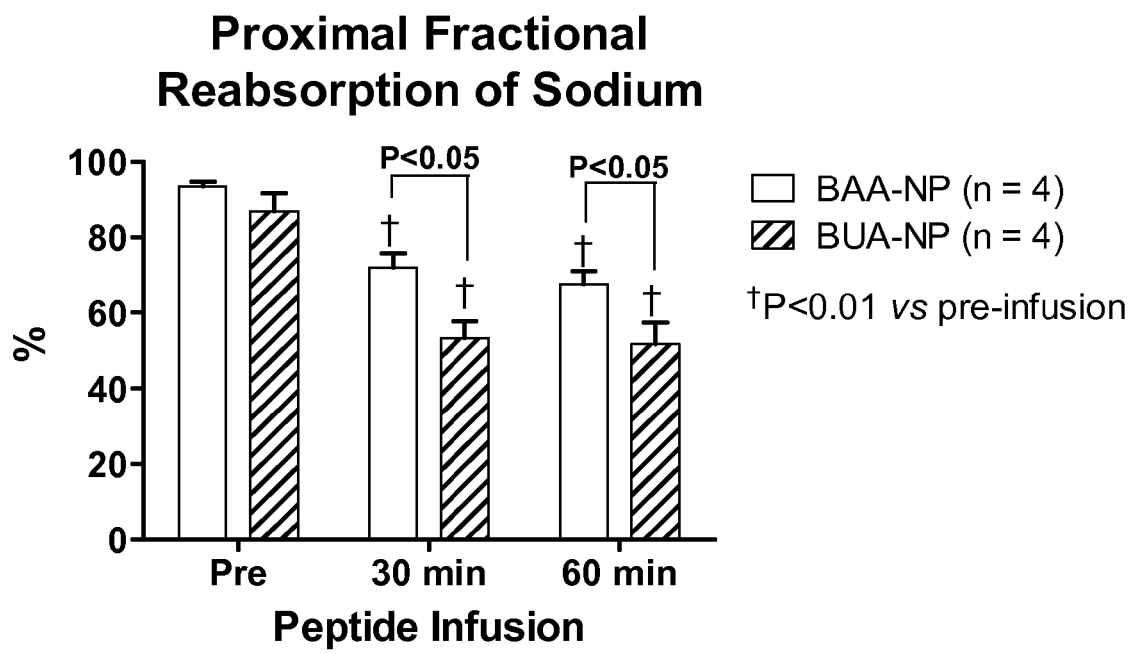
FIG. 70 is a graph plotting the proximal fractional reabsorption of sodium (%) before and after (30 minutes and 60 minutes) infusion with the indicated peptides.
Figure 71:
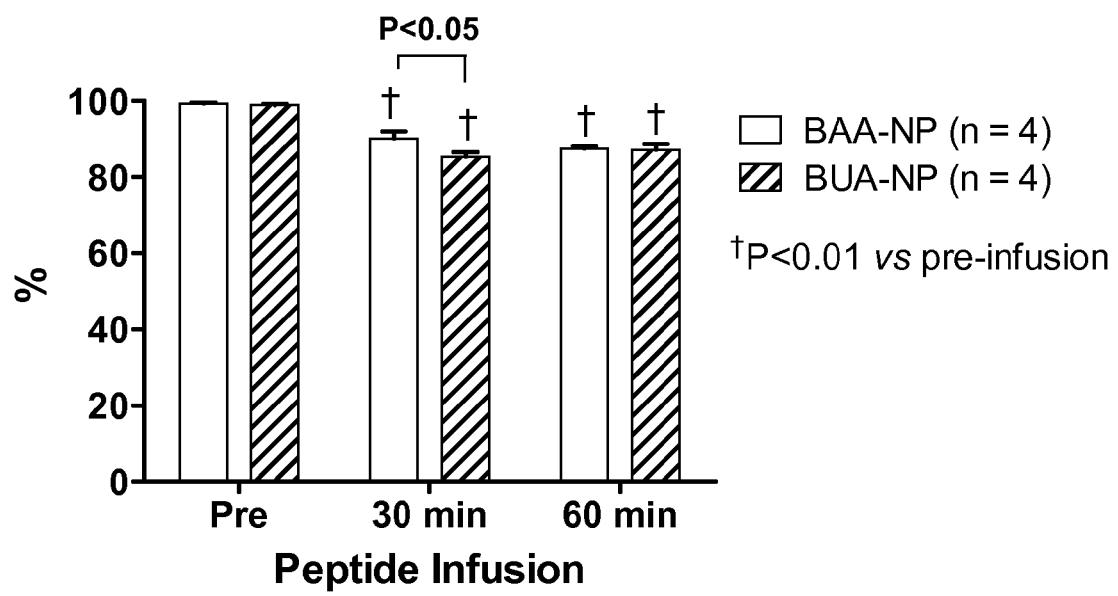
FIG. 71 is a graph plotting the distal fractional reabsorption of sodium (%) before and after (30 minutes and 60 minutes) infusion with the indicated peptides.
Figure 72:
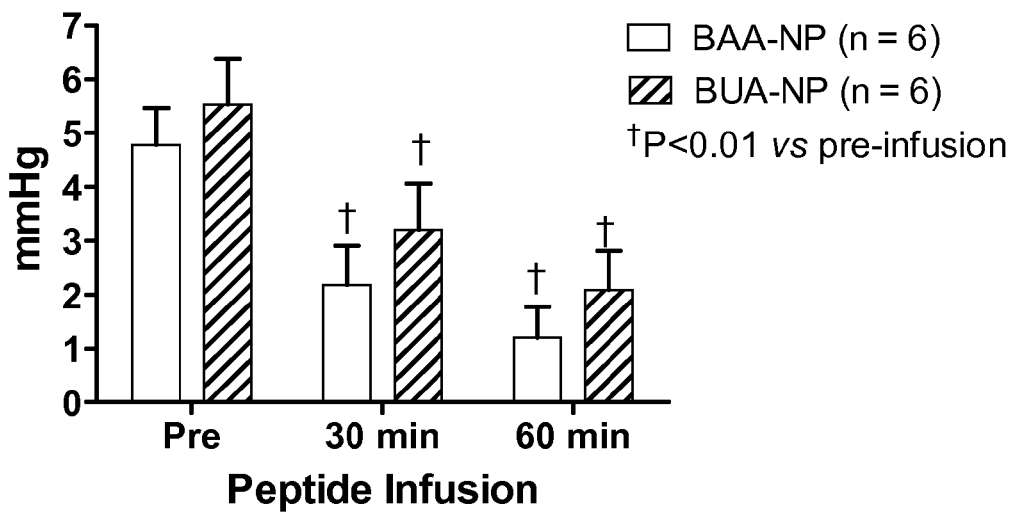
FIG. 72 is a graph plotting pulmonary capillary pressure (mmHg) before and after (30 minutes and 60 minutes) infusion with the indicated peptides.
Figure 73:
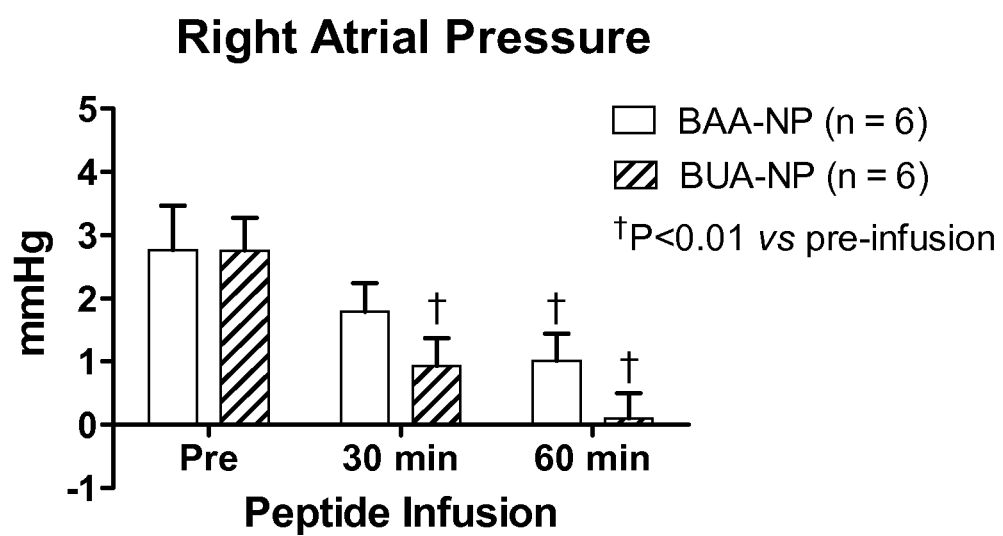
FIG. 73 is a graph plotting right arterial pressure (mmHg) before and after (30 minutes and 60 minutes) infusion with the indicated peptides.

The result using BAA-NP are set forth in FIGS. 3-29, and the results using BUA-NP are set forth in FIGS. 30-56. Comparisons with human BNP on mean arterial pressure and renal perfusion pressure are set forth in FIGS. 57 and 58. Additional analyses comparing changes in renal perfusion pressure from baseline and changes in mean arterial pressure from baseline among BAA-NP, BUA-NP, and BNP are set forth in FIGS. 59 to 62. Comparisons between BAA-NP and BUA-NP are set forth in FIGS. 63 to 73.

Both BAA-NP and BUA-NP significantly increased plasma cGMP, urinary cGMP excretion, net renal generation of cGMP, urine flow, and urinary sodium excretion. Both proximal and distal fractional reabsorption of sodium were significantly reduced. Urinary potassium excretion was also significantly increased. Glomerular filtration rate was preserved. Renal blood flow was significantly enhanced, and renal vascular resistance was significantly reduced. With BUA-NP, renal perfusion pressure was also preserved.

Both BAA-NP and BUA-NP significantly reduced pulmonary capillary pressure, right atrial pressure, and pulmonary arterial pressure. Cardiac output was preserved. A mild decrease in mean arterial pressure was detected.

Hemoconcentration was observed, as assessed by a significant increase in hematocrit. Plasma ANP and CNP immunreactivities were significantly increased. With BAA-NP, urinary excretion of ANP and CNP were also significantly increased. Plasma renin activity, angiotensin II, and aldosterone were significantly suppressed by BAA-NP.

When tested at an equimolar concentration, human BNP significantly reduced mean arterial pressure and renal perfusion pressure. Between group differences were not detected among BNP, BAA-NP, and BUA-NP.

When additional analyses were performed focusing on changes from baseline values, significantly greater decreases in renal perfusion pressure were observed with BNP, as compared to BAA-NP or BUA-NP, both at 30 minutes and at 60 minutes of infusion. In other words, both BAA-NP and BUA-NP, as compared to BNP, preserved renal perfusion pressure. With regard to changes in mean arterial pressure, a significantly greater reduction of mean arterial pressure from baseline was observed with BNP, as compared to BAA-NP or BUA-NP, at 30 minutes of infusion. This greater decrease in mean arterial pressure from baseline was also observed at 60 minutes of infusion with BNP versus BAA-NP. When the two natriuretic polypeptides, BUA-NP and BAA-NP, were compared, BUA-NP was observed to result in greater activation of cGMP, enhanced natriuresis and diuresis, and greater reductions in proximal and distal fractional reabsorption of sodium. Thus, fusion of the N-terminal tetrapeptide, TAPR, from the N-terminus of urodilatin to produce BUA-NP further enhanced the renal actions of BAA-NP. Overall, these results indicate that the engineered changes to the N- and C-termini of BNP provided herein can result in effective natriuretic polypeptides with enhanced pharmacologic profiles.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having a cardiovascular condition or renal condition, wherein said method comprises administering, to said mammal, a composition comprising a polypeptide under conditions wherein the severity of a manifestation of said cardiovascular condition or renal condition is reduced, wherein said polypeptide is less than 44 amino acid residues in length and comprises, in an order from amino terminus to carboxy terminus:
   (a) the sequence set forth in SEQ ID NO:6 or the sequence set forth in SEQ ID NO:6 with no more than two additions, subtractions, or substitutions,
   (b) the sequence set forth in SEQ ID NO:2 or the sequence set forth in SEQ ID NO:2 with no more than one addition, subtraction, or substitution, and
   (c) the sequence set forth in SEQ ID NO:7 or the sequence set forth in SEQ ID NO:7 with no more than two additions, subtractions, or substitutions.

2. The method of claim 1, wherein said polypeptide comprises natriuretic activity.

3. The method of claim 1, wherein said composition comprises a pharmaceutically acceptable carrier.

4. The method of claim 1, wherein said polypeptide comprises the sequence set forth in SEQ ID NO:6, the sequence set forth in SEQ ID NO:2, and the sequence set forth in SEQ ID NO:7.

5. The method of claim 1, wherein said polypeptide is a substantially pure polypeptide.

6. The method of claim 1, wherein said polypeptide comprises the sequence set forth in SEQ ID NO:6.

7. The method of claim 1, wherein said polypeptide comprises the sequence set forth in SEQ ID NO:6 with no more than two additions, subtractions, or substitutions.

8. The method of claim 1, wherein said polypeptide comprises the sequence set forth in SEQ ID NO:6 with one addition, subtraction, or substitution.

9. The method of claim 1, wherein said polypeptide comprises the sequence set forth in SEQ ID NO:2.

10. The method of claim 1, wherein said polypeptide comprises the sequence set forth in SEQ ID NO:2 with one addition, subtraction, or substitution.

11. The method of claim 1, wherein said polypeptide comprises the sequence set forth in SEQ ID NO:7.

12. The method of claim 1, wherein said polypeptide comprises the sequence set forth in SEQ ID NO:7 with no more than two additions, subtractions, or substitutions.

13. The method of claim 1, wherein said polypeptide comprises the sequence set forth in SEQ ID NO:7 with one addition, subtraction, or substitution.

14. The method of claim 1, wherein said polypeptide, when administered to a mammal, induces a decrease in mean arterial pressure to a lesser extent than that induced by human BNP, when said human BNP is administered to a mammal.

\* \* \* \* \*